(12) United States Patent
Chen et al.

(10) Patent No.: US 10,155,808 B2
(45) Date of Patent: Dec. 18, 2018

(54) MONOCLONAL ANTIBODY AGAINST HUMAN PRPC AND USE THEREOF

(71) Applicant: Institute of Zoology, Chinese Academy of Sciences, Beijing (CN)

(72) Inventors: Quan Chen, Beijing (CN); Baowei Li, Beijing (CN); Haiying Hang, Beijing (CN); Lei Du, Beijing (CN); Jun Wang, Beijing (CN); Xiaohui Wang, Beijing (CN)

(73) Assignee: Institute of Zoology, Chinese Academy of Sciences, Beijing (CN)

( * ) Notice: Subject to any disclaimer, the term of this patent is extended or adjusted under 35 U.S.C. 154(b) by 2 days.

(21) Appl. No.: 15/351,418

(22) Filed: Nov. 14, 2016

(65) Prior Publication Data

US 2017/0066817 A1 Mar. 9, 2017

Related U.S. Application Data

(63) Continuation-in-part of application No. PCT/CN2015/078775, filed on May 12, 2015.

(30) Foreign Application Priority Data

May 15, 2014 (CN) .......................... 2014 1 0206719

(51) Int. Cl.
| | | |
|---|---|---|
| *C07K 16/18* | (2006.01) | |
| *C07K 16/32* | (2006.01) | |
| *C07K 16/30* | (2006.01) | |
| *G01N 33/577* | (2006.01) | |
| *C07K 16/28* | (2006.01) | |
| *G01N 33/574* | (2006.01) | |
| *A61K 39/00* | (2006.01) | |

(52) U.S. Cl.
CPC .......... *C07K 16/18* (2013.01); *C07K 16/2863* (2013.01); *C07K 16/2872* (2013.01); *C07K 16/3046* (2013.01); *C07K 16/32* (2013.01); *G01N 33/577* (2013.01); *G01N 33/57492* (2013.01); *A61K 2039/505* (2013.01); *A61K 2039/507* (2013.01); *C07K 2317/24* (2013.01); *C07K 2317/34* (2013.01); *C07K 2317/55* (2013.01); *C07K 2317/56* (2013.01); *C07K 2317/73* (2013.01); *G01N 2333/47* (2013.01)

(58) Field of Classification Search
CPC ....... G01N 2800/2828; G01N 2333/47; G01N 33/57492; G01N 33/577; C07K 16/18; C07K 16/2863; C07K 16/3046; C07K 16/32; C07K 2317/24; C07K 2317/56; C07K 2317/73; C07K 2317/55; A61K 2039/505; A61K 2039/507
See application file for complete search history.

(56) References Cited

U.S. PATENT DOCUMENTS 6,261,790 B1 * 7/2001 O'Rourke .............. C07K 14/47
424/130.1

FOREIGN PATENT DOCUMENTS

| CN | 101550186 A | 10/2009 |
| CN | 103013927 | 4/2013 |
| CN | 104031148 | 9/2014 |

OTHER PUBLICATIONS

Alberts, Bruce et al. Molecular Biology of the Cell, Third Edition. Garland Publishing, Inc., New York, 1994, pp. 1216-1220.*
Kuby Janis, Immunology, Third Edition. WH Freeman & Co., New York 1997, pp. 131-135.*
State Intellectual Property Office of the People's Republic of China (ISR/CN), "International Search Report for PCT/CN2015/078775", China, dated Aug. 3, 2015.

* cited by examiner

*Primary Examiner* — Gregory S Emch
(74) *Attorney, Agent, or Firm* — Shuang Chang; PSK Intellectual Property Group, LLC

(57) ABSTRACT

A monoclonal antibody against human PrPc protein capable of reducing the expression level of transcription factor Twist1 in a targeting mode and inducing macrophage and NK cells to target to rectal cancer tumor cells. The combined drug therapy with the antibody and cetuximab also exhibits inhibitory effect on tumor better than administration of the antibody or cetuximab alone.

8 Claims, 8 Drawing Sheets

Specification includes a Sequence Listing.

```
                          SEQUENCE LISTING

<160> NUMBER OF SEQ ID NOS: 52

<210> SEQ ID NO 1
<211> LENGTH: 129
<212> TYPE: PRT
<213> ORGANISM: Mus musculus

<400> SEQUENCE: 1

Thr Met Glu Thr Asp Thr Leu Leu Trp Val Leu Leu Trp Val
 1               5                  10                  15

Pro Gly Ser Thr Gly Asp Ile Val Leu Thr Gln Ser Pro Ala Ser Leu
                20                  25                  30

Ala Val Ser Leu Gly Gln Arg Ala Thr Ile Ser Tyr Arg Ala Ser Lys
            35                  40                  45

Ser Val Ser Thr Ser Gly Tyr Ser Tyr Met His Trp Asn Gln Gln Lys
        50                  55                  60

Pro Gly Gln Pro Pro Arg Leu Leu Ile Tyr Leu Val Ser Asn Leu Glu
65                  70                  75                  80

Ser Gly Val Pro Ala Arg Phe Ser Gly Ser Gly Ser Gly Thr Asp Phe
                85                  90                  95

Thr Leu Asn Ile His Pro Val Glu Glu Asp Ala Ala Thr Tyr Tyr
                100                 105                 110

Cys Gln His Ile Arg Glu Leu Thr Arg Ser Glu Gly Gly Pro Ser Trp
            115                 120                 125

Lys

<210> SEQ ID NO 2
<211> LENGTH: 153
<212> TYPE: PRT
<213> ORGANISM: Mus musculus

<400> SEQUENCE: 2

Met Glu Cys Ser Trp Val Ile Leu Phe Leu Leu Ser Gly Thr Gly Gly
 1               5                  10                  15

Val Leu Ser Glu Val Gln Leu Gln Gln Ser Gly Pro Glu Leu Val Lys
                20                  25                  30

Pro Gly Ala Ser Val Lys Met Ser Cys Lys Ala Ser Gly Tyr Thr Phe
            35                  40                  45

Thr Asp Tyr Tyr Met Lys Trp Val Lys Gln Ser His Gly Lys Ser Leu
        50                  55                  60

Glu Trp Ile Gly Asp Ile Asn Pro Asn Asn Gly Asp Thr Phe Tyr Asn
65                  70                  75                  80

Gln Lys Phe Lys Gly Lys Ala Thr Leu Thr Val Asp Lys Ser Ser Asn
                85                  90                  95

Thr Ala Tyr Met Gln Leu Asn Ser Leu Thr Ser Glu Asp Ser Ala Val
                100                 105                 110

Tyr Tyr Cys Ala Lys Pro Gly Arg Thr Tyr Trp Gly Gln Gly Thr Leu
            115                 120                 125

Val Thr Val Ser Ala Ala Lys Thr Thr Ala Pro Ser Val Tyr Pro Leu
```

Ala Pro Val Cys Gly Gly Ser Arg Pro
145             150

<210> SEQ ID NO 3
<211> LENGTH: 388
<212> TYPE: DNA
<213> ORGANISM: Mus musculus

<400> SEQUENCE: 3
caccatggag acagacacac tcctgctatg ggtactgctg ctctgggttc caggttccac    60
tggtgacatt gtgctgacac agtctcctgc ttccttagct gtatctctgg ggcagagggc   120
caccatctca tacagggcca gcaaaagtgt cagtacatct ggctatagtt atatgcactg   180
gaaccaacag aaaccaggac agccacccag actcctcatc tatcttgtat ccaacctaga   240
atctggggtc cctgccaggt tcagtggcag tgggtctggg acagacttca ccctcaacat   300
ccatcctgtg gaggaggagg atgctgcaac ctattactgt cagcacatta gggagcttac   360
acgttcggag gggggaccaa gctggaaa                                      388

<210> SEQ ID NO 4
<211> LENGTH: 463
<212> TYPE: DNA
<213> ORGANISM: Mus musculus

<400> SEQUENCE: 4
caccatggaa tgcagctggg tcatcctctt tctcttgtca ggaactggag gtgtcctctc    60
tgaggtccaa ctgcaacagt ctggacctga gctggtgaag cctggggctt cagtgaagat   120
gtcctgcaag gcttctggat acaccttcac tgactactac atgaagtggg tgaagcagag   180
ccatggaaag agccttgagt ggattggaga tattaatcct aacaatggtg atactttcta   240
caaccagaag ttcaagggca aggccacatt gactgttgac aaatcctcca acacagccta   300
catgcagctc aacagcctga catctgagga ctctgcagtc tattactgtg caaaacctgg   360
gcggacttac tggggccaag ggactctggt cactgtctct gcagccaaaa caacagcccc   420
atcggtctat ccactggccc ctgtgtgtgg aggttctaga cct                     463

<210> SEQ ID NO 5
<211> LENGTH: 23
<212> TYPE: DNA
<213> ORGANISM: Artificial Sequence
<220> FEATURE:
<223> OTHER INFORMATION: positive-sense strand primer

<400> SEQUENCE: 5
ggatccatgg cgaaccttgg ctg                                            23

<210> SEQ ID NO 6
<211> LENGTH: 23
<212> TYPE: DNA
<213> ORGANISM: Artificial Sequence
<220> FEATURE:
<223> OTHER INFORMATION: antisense strand primer

<400> SEQUENCE: 6
ctcgagtccc actatcagga aga                                            23

<210> SEQ ID NO 7
<211> LENGTH: 759
<212> TYPE: DNA

<213> ORGANISM: Homo sapiens

<400> SEQUENCE: 7

```
atggcgaacc ttggctgctg gatgctggtt ctctttgtgg ccacatggag tgacctgggc      60
ctctgcaaga agcgcccgaa gcctggagga tggaacactg ggggcagccg atacccgggg     120
cagggcagcc ctggaggcaa ccgctaccca cctcagggcg gtggtggctg ggggcagcct     180
catggtggtg gctgggggca gcctcatggt ggtggctggg ggcagcccca tggtggtggc     240
tggggacagc ctcatggtgg tggctggggt caaggaggtg gcacccacag tcagtggaac     300
aagccgagta agccaaaaac caacatgaag cacatggctg gtgctgcagc agctggggca     360
gtggtggggg gccttggcgg ctacatgctg ggaagtgcca tgagcaggcc catcatacat     420
ttcggcagtg actatgagga ccgttactat cgtgaaaaca tgcaccgtta ccccaaccaa     480
gtgtactaca ggcccatgga tgagtacagc aaccagaaca actttgtgca cgactgcgtc     540
aatatcacaa tcaagcagca cacggtcacc acaaccacca aggggagaa cttcaccgag      600
accgacgtta agatgatgga gcgcgtggtt gagcagatgt gtatcaccca gtacgagagg     660
gaatctcagg cctattacca gagaggatcg agcatggtcc tcttctcctc tccacctgtg     720
atcctcctga tctctttcct catcttcctg atagtggga                            759
```

<210> SEQ ID NO 8
<211> LENGTH: 253
<212> TYPE: PRT
<213> ORGANISM: Homo sapiens

<400> SEQUENCE: 8

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 9
<211> LENGTH: 1049
<212> TYPE: DNA
<213> ORGANISM: Homo sapiens

<400> SEQUENCE: 9

| | |
|---|---|
| tcatcatcat tcttctggtc tggtgcacgc tgtgagcgga taacaattcc cctctagaaa | 60 |
| taattttgtt taactttaag aaggagatat acatatgcac catcatcatc atcattcttc | 120 |
| tggtctggtg ccacgcggtt ctggtatgaa agaaaccgct gctgctaaat tcgaacgcca | 180 |
| gcacatggac agcccagatc tgggtaccga cgacgacgac aaggccatgg ctgatatcgg | 240 |
| atccatggcg aaccttggct gctggatgct ggttctcttt gtggccacat ggagtgacct | 300 |
| gggcctctgc aagaagcgcc cgaagcctgg aggatggaac actgggggca gccgataccc | 360 |
| ggggcagggc agccctggag gcaaccgcta cccacctcag ggcggtggtg ctgggggca | 420 |
| gcctcatggt ggtggctggg gcagcctca tggtggtggc tgggggcagc cccatggtgg | 480 |
| tggctgggga cagcctcatg gtggtggctg gggtcaagga ggtggcaccc acagtcagtg | 540 |
| gaacaagccg agtaagccaa aaaccaacat gaagcacatg gctggtgctg cagcagctgg | 600 |
| ggcagtggtg gggggccttg gcggctacat gctgggaagt gccatgagca ggcccatcat | 660 |
| acatttcggc agtgactatg aggaccgtta ctatcgtgaa acatgcacc gttaccccaa | 720 |
| ccaagtgtac tacaggccca tggatgagta cagcaaccag aacaactttg tgcacgactg | 780 |
| cgtcaatatc acaatcaagc agcacacggt caccacaacc accaagggg agaacttcac | 840 |
| cgagaccgac gttaagatga tggagcgcgt ggttgagcag atgtgtatca cccagtacga | 900 |
| gagggaatct caggcctatt accagagagg atcgagcatg gtcctcttct cctctccacc | 960 |
| tgtgatcctc ctgatctctt tcctcatctt cctgatagtg ggactcgagc accaccacca | 1020 |
| ccaccactga gatccggctg caacaagca | 1049 |

<210> SEQ ID NO 10
<211> LENGTH: 26
<212> TYPE: DNA
<213> ORGANISM: Artificial Sequence
<220> FEATURE:
<223> OTHER INFORMATION: forward primer

<400> SEQUENCE: 10
ggggtaccat ggcgaacctt ggctgc                                         26

<210> SEQ ID NO 11
<211> LENGTH: 31
<212> TYPE: DNA
<213> ORGANISM: Artificial Sequence
<220> FEATURE:
<223> OTHER INFORMATION: reverse primer

<400> SEQUENCE: 11
ccgctcgagc ctcccactat caggaagatg a                                   31

<210> SEQ ID NO 12
<211> LENGTH: 150
<212> TYPE: PRT

<213> ORGANISM: Homo sapiens

<400> SEQUENCE: 12

Ala Thr Gly Gly Cys Gly Ala Ala Cys Cys Thr Gly Gly Cys Thr
1               5                   10                  15

Gly Cys Thr Gly Gly Ala Thr Cys Thr Gly Thr Thr Cys Thr
            20                  25                  30

Cys Thr Thr Thr Gly Thr Gly Gly Cys Cys Ala Cys Thr Gly Gly
        35                  40                  45

Ala Gly Thr Gly Ala Cys Cys Thr Gly Gly Cys Cys Thr Cys Thr
    50                  55                  60

Gly Cys Ala Ala Gly Ala Ala Gly Cys Gly Cys Cys Cys Gly Ala Ala
65                  70                  75                  80

Gly Cys Cys Thr Gly Gly Ala Gly Gly Ala Thr Gly Gly Ala Ala Cys
                85                  90                  95

Ala Cys Thr Gly Gly Gly Gly Gly Cys Ala Gly Cys Cys Gly Ala Thr
                100                 105                 110

Ala Cys Cys Cys Gly Gly Gly Cys Ala Gly Gly Gly Cys Ala Gly
            115                 120                 125

Cys Cys Cys Thr Gly Gly Ala Gly Gly Cys Ala Ala Cys Cys Gly Cys
        130                 135                 140

Thr Ala Cys Cys Cys Ala
145                 150

<210> SEQ ID NO 13
<211> LENGTH: 50
<212> TYPE: PRT
<213> ORGANISM: Homo sapiens

<400> SEQUENCE: 13

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro
    50

<210> SEQ ID NO 14
<211> LENGTH: 40
<212> TYPE: DNA
<213> ORGANISM: Artificial Sequence
<220> FEATURE:
<223> OTHER INFORMATION: forward primer

<400> SEQUENCE: 14
ggcaaccgct acccaggacg agctcagatc tcccgggcgc                              40

<210> SEQ ID NO 15
<211> LENGTH: 40
<212> TYPE: DNA
<213> ORGANISM: Artificial Sequence
<220> FEATURE:
<223> OTHER INFORMATION: reverse primer

<400> SEQUENCE: 15
ctagactcga gctcctgggt agcggttgcc tccagggctg                              40

<210> SEQ ID NO 16
<211> LENGTH: 609
<212> TYPE: DNA
<213> ORGANISM: Homo sapiens

<400> SEQUENCE: 16

```
cctcagggcg gtggtggctg ggggcagcct catggtggtg gctggggca gcctcatggt       60
ggtggctggg ggcagcccca tggtggtggc tgggacagc ctcatggtgg tggctggggt      120
caaggaggtg gcacccacag tcagtggaac aagccgagta agccaaaaac caacatgaag      180
cacatggctg gtgctgcagc agctggggca gtggtgggg gccttggcgg ctacatgctg      240
ggaagtgcca tgagcaggcc catcatacat ttcggcagtg actatgagga ccgttactat      300
cgtgaaaaca tgcaccgtta ccccaaccaa gtgtactaca ggcccatgga tgagtacagc      360
aaccagaaca actttgtgca cgactgcgtc aatatcacaa tcaagcagca cacggtcacc      420
acaaccacca agggggagaa cttcaccgag accgacgtta agatgatgga gcgcgtggtt      480
gagcagatgt gtatcaccca gtacgagagg gaatctcagg cctattacca gagaggatcg      540
agcatggtcc tcttctcctc tccacctgtg atcctcctga tctcttctcct catcttcctg      600
atagtggga                                                              609
```

<210> SEQ ID NO 17
<211> LENGTH: 203
<212> TYPE: PRT
<213> ORGANISM: Homo sapiens

<400> SEQUENCE: 17

```
Pro Gln Gly Gly Gly Gly Trp Gly Gln Pro His Gly Gly Gly Trp Gly
1               5                   10                  15

Gln Pro His Gly Gly Gly Trp Gly Gln Pro His Gly Gly Gly Trp Gly
            20                  25                  30

Gln Pro His Gly Gly Gly Trp Gly Gln Gly Gly Gly Thr His Ser Gln
        35                  40                  45

Trp Asn Lys Pro Ser Lys Pro Lys Thr Asn Met Lys His Met Ala Gly
    50                  55                  60

Ala Ala Ala Ala Gly Ala Val Val Gly Gly Leu Gly Gly Tyr Met Leu
65                  70                  75                  80

Gly Ser Ala Met Ser Arg Pro Ile Ile His Phe Gly Ser Asp Tyr Glu
                85                  90                  95

Asp Arg Tyr Tyr Arg Glu Asn Met His Arg Tyr Pro Asn Gln Val Tyr
            100                 105                 110

Tyr Arg Pro Met Asp Glu Tyr Ser Asn Gln Asn Asn Phe Val His Asp
        115                 120                 125

Cys Val Asn Ile Thr Ile Lys Gln His Thr Val Thr Thr Thr Thr Lys
    130                 135                 140

Gly Glu Asn Phe Thr Glu Thr Asp Val Lys Met Met Glu Arg Val Val
145                 150                 155                 160

Glu Gln Met Cys Ile Thr Gln Tyr Glu Arg Glu Ser Gln Ala Tyr Tyr
                165                 170                 175

Gln Arg Gly Ser Ser Met Val Leu Phe Ser Ser Pro Pro Val Ile Leu
            180                 185                 190

Leu Ile Ser Phe Leu Ile Phe Leu Ile Val Gly
        195                 200
```

<210> SEQ ID NO 18
<211> LENGTH: 40

```
<212> TYPE: DNA
<213> ORGANISM: Artificial Sequence
<220> FEATURE:
<223> OTHER INFORMATION: forward primer

<400> SEQUENCE: 18
aagcttggta ccatgcctca gggcggtggt ggctgggggc                                40

<210> SEQ ID NO 19
<211> LENGTH: 40
<212> TYPE: DNA
<213> ORGANISM: Artificial Sequence
<220> FEATURE:
<223> OTHER INFORMATION: reverse primer

<400> SEQUENCE: 19
accaccgccc tgaggcatgg taccaagctt aactagccag                                40

<210> SEQ ID NO 20
<211> LENGTH: 444
<212> TYPE: DNA
<213> ORGANISM: Homo sapiens

<400> SEQUENCE: 20
aaaaccaaca tgaagcacat ggctggtgct gcagcagctg ggcagtggt gggggggcctt         60 ggcggctaca tgctgggaag tgccatgagc aggcccatca tacatttcgg cagtgactat        120
gaggaccgtt actatcgtga aaacatgcac cgttacccca accaagtgta ctacaggccc        180
atggatgagt acagcaacca gaacaacttt gtgcacgact gcgtcaatat cacaatcaag        240
cagcacacgg tcaccacaac caccaagggg gagaacttca ccgagaccga cgttaagatg        300
atggagcgcg tggttgagca gatgtgtatc acccagtacg agagggaatc tcaggcctat        360
taccagagag gatcgagcat ggtcctcttc tcctctccac ctgtgatcct cctgatctct        420
ttcctcatct tcctgatagt ggga                                               444

<210> SEQ ID NO 21
<211> LENGTH: 148
<212> TYPE: PRT
<213> ORGANISM: Homo sapiens

<400> SEQUENCE: 21

Lys Thr Asn Met Lys His Met Ala Gly Ala Ala Ala Gly Ala Val
1               5                   10                  15

Val Gly Gly Leu Gly Gly Tyr Met Leu Gly Ser Ala Met Ser Arg Pro
            20                  25                  30

Ile Ile His Phe Gly Ser Asp Tyr Glu Asp Arg Tyr Tyr Arg Glu Asn
        35                  40                  45

Met His Arg Tyr Pro Asn Gln Val Tyr Tyr Arg Pro Met Asp Glu Tyr
    50                  55                  60

Ser Asn Gln Asn Asn Phe Val His Asp Cys Val Asn Ile Thr Ile Lys
65                  70                  75                  80

Gln His Thr Val Thr Thr Thr Thr Lys Gly Glu Asn Phe Thr Glu Thr
                85                  90                  95

Asp Val Lys Met Met Glu Arg Val Glu Gln Met Cys Ile Thr Gln
            100                 105                 110

Tyr Glu Arg Glu Ser Gln Ala Tyr Tyr Gln Arg Gly Ser Ser Met Val
        115                 120                 125

Leu Phe Ser Ser Pro Pro Val Ile Leu Leu Ile Ser Phe Leu Ile Phe
    130                 135                 140
```

Leu Ile Val Gly
145

<210> SEQ ID NO 22
<211> LENGTH: 40
<212> TYPE: DNA
<213> ORGANISM: Artificial Sequence
<220> FEATURE:
<223> OTHER INFORMATION: forward primer

<400> SEQUENCE: 22
aagcttggta ccatgaaaac caacatgaag cacatggctg                40

<210> SEQ ID NO 23
<211> LENGTH: 40
<212> TYPE: DNA
<213> ORGANISM: Artificial Sequence
<220> FEATURE:
<223> OTHER INFORMATION: reverse primer

<400> SEQUENCE: 23
cttcatgttg gttttcatgg taccaagctt aactagccag                40

<210> SEQ ID NO 24
<211> LENGTH: 381
<212> TYPE: DNA
<213> ORGANISM: Homo sapiens

<400> SEQUENCE: 24
ggctacatgc tgggaagtgc catgagcagg cccatcatac atttcggcag tgactatgag      60
gaccgttact atcgtgaaaa catgcaccgt taccccaacc aagtgtacta caggcccatg     120
gatgagtaca gcaaccagaa caactttgtg cacgactgcg tcaatatcac aatcaagcag     180
cacacggtca ccacaaccac caaggggag aacttcaccg agaccgacgt taagatgatg      240
gagcgcgtgg ttgagcagat gtgtatcacc cagtacgaga gggaatctca ggcctattac     300
cagagaggat cgagcatggt cctcttctcc tctccacctg tgatcctcct gatctctttc     360
ctcatcttcc tgatagtggg a                                               381

<210> SEQ ID NO 25
<211> LENGTH: 127
<212> TYPE: PRT
<213> ORGANISM: Homo sapiens

<400> SEQUENCE: 25

Gly Tyr Met Leu Gly Ser Ala Met Ser Arg Pro Ile Ile His Phe Gly
1               5                   10                  15
Ser Asp Tyr Glu Asp Arg Tyr Tyr Arg Glu Asn Met His Arg Tyr Pro
            20                  25                  30
Asn Gln Val Tyr Tyr Arg Pro Met Asp Glu Tyr Ser Asn Gln Asn Asn
        35                  40                  45
Phe Val His Asp Cys Val Asn Ile Thr Ile Lys Gln His Thr Val Thr
    50                  55                  60
Thr Thr Thr Lys Gly Glu Asn Phe Thr Glu Thr Asp Val Lys Met Met
65                  70                  75                  80
Glu Arg Val Val Glu Gln Met Cys Ile Thr Gln Tyr Glu Arg Glu Ser
                85                  90                  95
Gln Ala Tyr Tyr Gln Arg Gly Ser Ser Met Val Leu Phe Ser Ser Pro
            100                 105                 110

-continued

```
Pro Val Ile Leu Leu Ile Ser Phe Leu Ile Phe Leu Ile Val Gly
        115                 120                 125
```

<210> SEQ ID NO 26
<211> LENGTH: 40
<212> TYPE: DNA
<213> ORGANISM: Artificial Sequence
<220> FEATURE:
<223> OTHER INFORMATION: forward primer

<400> SEQUENCE: 26
aagcttggta ccatgggcta catgctggga agtgccatga                40

<210> SEQ ID NO 27
<211> LENGTH: 40
<212> TYPE: DNA
<213> ORGANISM: Artificial Sequence
<220> FEATURE:
<223> OTHER INFORMATION: reverse primer

<400> SEQUENCE: 27
tcccagcatg tagcccatgg taccaagctt aactagccag                40

<210> SEQ ID NO 28
<211> LENGTH: 330
<212> TYPE: DNA
<213> ORGANISM: Homo sapiens

<400> SEQUENCE: 28
gactatgagg accgttacta tcgtgaaaac atgcaccgtt accccaacca agtgtactac    60
aggcccatgg atgagtacag caaccagaac aactttgtgc acgactgcgt caatatcaca   120
atcaagcagc acacggtcac cacaaccacc aaggggagaa acttcaccga gaccgacgtt   180
aagatgatgg agcgcgtggt tgagcagatg tgtatcaccc agtacgagag ggaatctcag   240
gcctattacc agagaggatc gagcatggtc ctcttctcct ctccacctgt gatcctcctg   300
atctctttcc tcatcttcct gatagtggga                                    330

<210> SEQ ID NO 29
<211> LENGTH: 110
<212> TYPE: PRT
<213> ORGANISM: Homo sapiens

<400> SEQUENCE: 29

```
Asp Tyr Glu Asp Arg Tyr Tyr Arg Glu Asn Met His Arg Tyr Pro Asn
1               5                   10                  15
Gln Val Tyr Tyr Arg Pro Met Asp Glu Tyr Ser Asn Gln Asn Asn Phe
            20                  25                  30
Val His Asp Cys Val Asn Ile Thr Ile Lys Gln His Thr Val Thr Thr
        35                  40                  45
Thr Thr Lys Gly Glu Asn Phe Thr Glu Thr Asp Val Lys Met Met Glu
    50                  55                  60
Arg Val Val Glu Gln Met Cys Ile Thr Gln Tyr Glu Arg Glu Ser Gln
65                  70                  75                  80
Ala Tyr Tyr Gln Arg Gly Ser Ser Met Val Leu Phe Ser Ser Pro Pro
                85                  90                  95
Val Ile Leu Leu Ile Ser Phe Leu Ile Phe Leu Ile Val Gly
            100                 105                 110
```

<210> SEQ ID NO 30
<211> LENGTH: 40

```
<212> TYPE: DNA
<213> ORGANISM: Artificial Sequence
<220> FEATURE:
<223> OTHER INFORMATION: forward primer

<400> SEQUENCE: 30
aagcttggta ccatggacta tgaggaccgt tactatcgtg                                40

<210> SEQ ID NO 31
<211> LENGTH: 40
<212> TYPE: DNA
<213> ORGANISM: Artificial Sequence
<220> FEATURE:
<223> OTHER INFORMATION: reverser primer

<400> SEQUENCE: 31
acggtcctca tagtccatgg taccaagctt aactagccag                                40

<210> SEQ ID NO 32
<211> LENGTH: 282
<212> TYPE: DNA
<213> ORGANISM: Homo sapiens

<400> SEQUENCE: 32
caagtgtact acaggcccat ggatgagtac agcaaccaga caactttgt gcacgactgc           60 gtcaatatca caatcaagca gcacacggtc accacaacca ccaagggga gaacttcacc          120 gagaccgacg ttaagatgat ggagcgcgtg gttgagcaga tgtgtatcac ccagtacgag         180
agggaatctc aggcctatta ccagagagga tcgagcatgg tcctcttctc ctctccacct         240
gtgatcctcc tgatctcttt cctcatcttc ctgatagtgg ga                            282

<210> SEQ ID NO 33
<211> LENGTH: 94
<212> TYPE: PRT
<213> ORGANISM: Homo sapiens

<400> SEQUENCE: 33

Gln Val Tyr Tyr Arg Pro Met Asp Glu Tyr Ser Asn Gln Asn Asn Phe
1               5                   10                  15

Val His Asp Cys Val Asn Ile Thr Ile Lys Gln His Thr Val Thr Thr
                20                  25                  30

Thr Thr Lys Gly Glu Asn Phe Thr Glu Thr Asp Val Lys Met Met Glu
            35                  40                  45

Arg Val Val Glu Gln Met Cys Ile Thr Gln Tyr Glu Arg Glu Ser Gln
        50                  55                  60

Ala Tyr Tyr Gln Arg Gly Ser Ser Met Val Leu Phe Ser Ser Pro Pro
65                  70                  75                  80

Val Ile Leu Leu Ile Ser Phe Leu Ile Phe Leu Ile Val Gly
                85                  90

<210> SEQ ID NO 34
<211> LENGTH: 40
<212> TYPE: DNA
<213> ORGANISM: Artificial Sequence
<220> FEATURE:
<223> OTHER INFORMATION: forward primer

<400> SEQUENCE: 34
aagcttggta ccatgcaagt gtactacagg cccatggatg                                40

<210> SEQ ID NO 35
```

```
<211> LENGTH: 40
<212> TYPE: DNA
<213> ORGANISM: Artificial Sequence
<220> FEATURE:
<223> OTHER INFORMATION: reverse primer

<400> SEQUENCE: 35
cctgtagtac acttgcatgg taccaagctt aactagccag                      40

<210> SEQ ID NO 36
<211> LENGTH: 246
<212> TYPE: DNA
<213> ORGANISM: Homo sapiens

<400> SEQUENCE: 36
cagaacaact ttgtgcacga ctgcgtcaat atcacaatca agcagcacac ggtcaccaca  60
accaccaagg gggagaactt caccgagacc gacgttaaga tgatggagcg cgtggttgag  120
cagatgtgta tcacccagta cgagagggaa tctcaggcct attaccagag aggatcgagc  180
atggtcctct ctcctctccc acctgtgatc ctcctgatct ctttcctcat cttcctgata  240
gtggga                                                            246

<210> SEQ ID NO 37
<211> LENGTH: 82
<212> TYPE: PRT
<213> ORGANISM: Homo sapiens

<400> SEQUENCE: 37

Gln Asn Asn Phe Val His Asp Cys Val Asn Ile Thr Ile Lys Gln His
1               5                   10                  15

Thr Val Thr Thr Thr Thr Lys Gly Glu Asn Phe Thr Glu Thr Asp Val
            20                  25                  30

Lys Met Met Glu Arg Val Val Glu Gln Met Cys Ile Thr Gln Tyr Glu
        35                  40                  45

Arg Glu Ser Gln Ala Tyr Tyr Gln Arg Gly Ser Ser Met Val Leu Phe
    50                  55                  60

Ser Ser Pro Pro Val Ile Leu Leu Ile Ser Phe Leu Ile Phe Leu Ile
65                  70                  75                  80

Val Gly

<210> SEQ ID NO 38
<211> LENGTH: 40
<212> TYPE: DNA
<213> ORGANISM: Artificial Sequence
<220> FEATURE:
<223> OTHER INFORMATION: aagcttggta ccatgcagaa caactttgtg cacgactgcg

<400> SEQUENCE: 38
aagcttggta ccatgcagaa caactttgtg cacgactgcg                      40

<210> SEQ ID NO 39
<211> LENGTH: 40
<212> TYPE: DNA
<213> ORGANISM: Artificial Sequence
<220> FEATURE:
<223> OTHER INFORMATION: reverse primer

<400> SEQUENCE: 39
cacaaagttg ttctgcatgg taccaagctt aactagccag                      40

<210> SEQ ID NO 40
```

<211> LENGTH: 177
<212> TYPE: DNA
<213> ORGANISM: Homo sapiens

<400> SEQUENCE: 40

```
ggggagaact tcaccgagac cgacgttaag atgatggagc gcgtggttga gcagatgtgt    60
atcacccagt acgagaggga atctcaggcc tattaccaga gaggatcgag catggtcctc   120
ttctcctctc cacctgtgat cctcctgatc tctttcctca tcttcctgat agtggga       177
```

<210> SEQ ID NO 41
<211> LENGTH: 59
<212> TYPE: PRT
<213> ORGANISM: Homo sapiens

<400> SEQUENCE: 41

```
Gly Glu Asn Phe Thr Glu Thr Asp Val Lys Met Met Glu Arg Val Val
1               5                   10                  15

Glu Gln Met Cys Ile Thr Gln Tyr Glu Arg Glu Ser Gln Ala Tyr Tyr
            20                  25                  30

Gln Arg Gly Ser Ser Met Val Leu Phe Ser Ser Pro Val Ile Leu
        35                  40                  45

Leu Ile Ser Phe Leu Ile Phe Leu Ile Val Gly
    50                  55
```

<210> SEQ ID NO 42
<211> LENGTH: 40
<212> TYPE: DNA
<213> ORGANISM: Artificial Sequence
<220> FEATURE:
<223> OTHER INFORMATION: forward primer

<400> SEQUENCE: 42

```
aagcttggta ccatggggga gaacttcacc gagaccgacg                           40
```

<210> SEQ ID NO 43
<211> LENGTH: 40
<212> TYPE: DNA
<213> ORGANISM: Artificial Sequence
<220> FEATURE:
<223> OTHER INFORMATION: reverse primer

<400> SEQUENCE: 43

```
ggtgaagttc tcccccatgg taccaagctt aactagccag                           40
```

<210> SEQ ID NO 44
<211> LENGTH: 69
<212> TYPE: DNA
<213> ORGANISM: Homo sapiens

<400> SEQUENCE: 44

```
agcatggtcc tcttctcctc tccacctgtg atcctcctga tctctttcct catcttcctg    60
atagtggga                                                             69
```

<210> SEQ ID NO 45
<211> LENGTH: 23
<212> TYPE: PRT
<213> ORGANISM: Homo sapiens

<400> SEQUENCE: 45

```
Ser Met Val Leu Phe Ser Ser Pro Val Ile Leu Leu Ile Ser Phe
1               5                   10                  15
```

```
Leu Ile Phe Leu Ile Val Gly
            20
```

<210> SEQ ID NO 46
<211> LENGTH: 40
<212> TYPE: DNA
<213> ORGANISM: Artificial Sequence
<220> FEATURE:
<223> OTHER INFORMATION: forward primer

<400> SEQUENCE: 46
aagcttggta ccatgagcat ggtcctcttc tcctctccac     40

<210> SEQ ID NO 47
<211> LENGTH: 40
<212> TYPE: DNA
<213> ORGANISM: Artificial Sequence
<220> FEATURE:
<223> OTHER INFORMATION: reverse primer

<400> SEQUENCE: 47
gaagaggacc atgctcatgg taccaagctt aactagccag     40

<210> SEQ ID NO 48
<211> LENGTH: 35
<212> TYPE: PRT
<213> ORGANISM: Homo sapiens

<400> SEQUENCE: 48

```
Gly Tyr Met Leu Gly Ser Ala Met Ser Arg Pro Ile Ile His Phe Gly
1               5                   10                  15

Ser Asp Tyr Glu Asp Arg Tyr Tyr Arg Glu Asn Met His Arg Tyr Pro
            20                  25                  30

Asn Gln Val
        35
```

<210> SEQ ID NO 49
<211> LENGTH: 63
<212> TYPE: DNA
<213> ORGANISM: Artificial Sequence
<220> FEATURE:
<223> OTHER INFORMATION: RNAi primer

<400> SEQUENCE: 49
gatccgccga gtaagccaaa aaccttcaag agaggttttt ggcttactcg gcttttttgg     60
aaa     63

<210> SEQ ID NO 50
<211> LENGTH: 63
<212> TYPE: DNA
<213> ORGANISM: Artificial Sequence
<220> FEATURE:
<223> OTHER INFORMATION: RNAi primer

<400> SEQUENCE: 50
agcttttcca aaaaagccga gtaagccaaa aacctctctt gaaggttttt ggcttactcg     60
gcg     63

<210> SEQ ID NO 51
<211> LENGTH: 64
<212> TYPE: DNA
<213> ORGANISM: Artificial Sequence
<220> FEATURE:
<223> OTHER INFORMATION: RNAi primer

```
<400> SEQUENCE: 51
gatccgcgca ggatacgcaa cacacctcaa gagagtgtgt tgcgtatcct gcgtttttg    60 gaaa                                                                 64

<210> SEQ ID NO 52
<211> LENGTH: 64
<212> TYPE: DNA
<213> ORGANISM: Artificial Sequence
<220> FEATURE:
<223> OTHER INFORMATION: RNAi primer

<400> SEQUENCE: 52
agcttttcca aaaacgcag gatacgcaac acactctctt gaggtgtgtt gcgtatcctg    60
cgcg                                                                 64
```

MONOCLONAL ANTIBODY AGAINST HUMAN PRPC AND USE THEREOF

CROSS-REFERENCE TO RELATED APPLICATIONS

This application is a continuation-in-part application of International Patent Application No. PCT/CN2015/078775, filed May 12, 2015, which itself claims priority to and benefit of, under 35 U.S.C. § 119(a), Patent Application No. 201410206719.0 filed in P.R. China on May 15, 2014, which are incorporated herein by reference in their entireties.

FIELD OF THE INVENTION

The present invention relates to a monoclonal antibody against human cellular prion protein (PrPc) and use thereof.

BACKGROUND OF THE INVENTION

Colorectal cancer is a common malignant tumor, and the third lethal tumor in the world. In the developed western countries, colorectal cancer gets morbidity at second place following lung cancer. In China, the morbidity and mortality of colorectal cancer also show an ascending trend from the sixth place in 1980s to the fourth place at present.

Targeted therapy of tumors is a newly developed method for treatment of cancers, which avoid to a great extent in spread of tumors and serious toxic and side-effects caused by conventional cancer therapies such as operative treatment, chemotherapy and radiotherapy. Monoclonal antibody therapy aiming at tumor cell surface antigens is a main targeted therapy for tumors and exhibits good oncotherapy effects.

Cellular prion protein (PrPc) is a glycoprotein widely expressed on surface of eukaryotic cells, which has 253 amino acids, a glycosylphosphatidylinositol (GPI) binding site at C-terminal for docking at outer membrane of cells, and two aspartate residues at sites 181 and 197 as glycosylation sites. In a mammal, PrPc is mainly expressed in nervous system, but also expressed in non-neural tissues such as lymphocytes, gastric epithelial cells, kidney cells, and muscles. In some reports, PrPc relates to tumorigenesis and drug-resistance, and it is highly expressed in cancer tissues of many cancers such as colorectal cancer, prostate cancer, gastric cancer, etc. The preliminary work of the present invention also shows that the cells with co-expression of CD44 and PrPc have features of tumor stem cells. In addition, some reports state that PrPc also plays an important role in hepatic metastases of colorectal cancer stem cells. Hence, researches of targeted therapy aiming at PrPc on the basis of monoclonal antibody are promising in providing a new therapy for cancer treatments.

SUMMARY OF THE INVENTION

The present invention relates to a monoclonal antibody Ab-5 specifically binding to human cellular prion protein (PrPc).

The Ab-5 antibody has a light chain variable region (VL) with an amino acid sequence as shown in SEQ ID NO:1, a heavy chain variable (VH) with an amino acid sequence as shown in SEQ ID NO:2, and a constant region derived from a murine constant region.

SEQ ID NO: 1:
TMETDTLLLWVLLLWVPGSTGDIVLTQSPASLAVSLGQRATISYRASKSV

STSGYSYMHWNQQKPGQPPRLLIYLVSNLESGVPARFSGSGSGTDFTLN

IHPVEEEDAATYYCQHIRELTRSEGGPSWK

SEQ ID NO: 2:
MECSWVILFLLSGTGGVLSEVQLQQSGPELVKPGASVKMSCKASGYTFT

DYYMKWVKQSHGKSLEWIGDINPNNGDTFYNQKFKGKATLTVDKSSNTAY

MQLNSLTSEDSAVYYCAKPGRTYWGQGTLVTVSAAKTTAPSVYPLAPVC

GGSRP

The present invention further relates to a nucleotide sequence encoding the Ab-5 antibody. The light chain encoding sequence of the Ab-5 antibody is preferably SEQ ID NO:3, and the heavy chain encoding sequence of the Ab-5 antibody is preferably SEQ ID NO:4.

SEQ ID NO: 3:
CACCATGGAGACAGACACACTCCTGCTATGGGTACTGCTGCTCTGGGT

TCCAGGTTCCACTGGTGACATTGTGCTGACACAGTCTCCTGCTTCCTT

AGCTGTATCTCTGGGGCAGAGGGCCACCATCTCATACAGGGCCAGCA

AAAGTGTCAGTACATCTGGCTATAGTTATATGCACTGGAACCAACAGAA

ACCAGGACAGCCACCCAGACTCCTCATCTATCTTGTATCCAACCTAGA

ATCTGGGGTCCCTGCCAGGTTCAGTGGCAGTGGGTCTGGGACAGACTT

CACCCTCAACATCCATCCTGTGGAGGAGGAGGATGCTGCAACCTATTA

CTGTCAGCACATTAGGGAGCTTACACGTTCGGAGGGGGGACCAAGCT

GGAAA

SEQ ID NO: 4:
CACCATGGAATGCAGCTGGGTCATCCTCTTTCTCTTGTCAGGAACTGG

AGGTGTCCTCTCTGAGGTCCAACTGCAACAGTCTGGACCTGAGCTGGTG

AAGCCTGGGGCTTCAGTGAAGATGTCCTGCAAGGCTTCTGGATACACC

TTCACTGACTACTACATGAAGTGGGTGAAGCAGAGCCATGGAAAGAGC

CTTGAGTGGATTGGAGATATTAATCCTAACAATGGTGATACTTTCTACA

ACCAGAAGTTCAAGGGCAAGGCCACATTGACTGTTGACAAATCCTCCA

ACACAGCCTACATGCAGCTCAACAGCCTGACATCTGAGGACTCTGCAG

TCTATTACTGTGCAAAACCTGGGCGGACTTACTGGGGCCAAGGGACTC

TGGTCACTGTCTCTGCAGCCAAAACAACAGCCCCATCGGTCTATCCAC

TGGCCCCTGTGTGTGGAGGTTCTAGACCT

The present invention further relates to an anti-PrPc antibody obtained by a humanization improvement or a complete humanization improvement of antibody based on a Fab fragment of the Ab-5 antibody.

The anti-PrPc antibody Ab-5 is deposited in China General Microbiological Culture Collection Center (CGMCC) on Mar. 19, 2018 with a CGMCC depository No. 15490.

The present invention further relates to a use of the Ab-5 antibody, the humanization improved/complete humanization improved Ab-5 antibody or active fragments, encoding genes thereof in manufacture of a detection reagent or diagnosis reagent for detecting PrPc protein.

The present invention further relates to a detection kit for PrPc protein which comprises the Ab-5 antibody, the humanization improved/complete humanization improved Ab-5 antibody or active fragments, encoding genes thereof as main components.

The present invention further relates to a use of the Ab-5 antibody, the humanization improved/complete humanization improved Ab-5 antibody or active fragments, encoding genes thereof in manufacture of a medicament, in which the medicament is an antitumor drug or a drug for inhibition of tumor metastasis, and the tumor is preferably selected from solid tumors, most preferably selected from colorectal cancer, prostate cancer, gastric cancer and breast cancer.

The present invention further relates to an anti-tumor drug, comprising the Ab-5 antibody, the humanization improved/complete humanization improved Ab-5 antibody or active fragments, encoding genes thereof as main active component, in which the tumor is preferably selected from solid tumors, most preferably selected from colorectal cancer, prostate cancer, gastric cancer and breast cancer.

The present invention further relates to a use of the Ab-5 antibody, the humanization improved/complete humanization improved Ab-5 antibody or active fragments, encoding genes thereof as a synergistic adjuvant for an existing antitumor drug, in which the tumor is preferably selected from solid tumors, most preferably selected from colorectal cancer, prostate cancer, gastric cancer and breast cancer, and the antitumor drug is preferably cetuximab.

The present invention further relates to an anti-tumor composition, comprising the Ab-5 antibody, the humanization improved/complete humanization improved Ab-5 antibody or active fragments, encoding genes thereof and an existing antitumor drug, in which the tumor is preferably selected from solid tumors, most preferably selected from colorectal cancer, prostate cancer, gastric cancer and breast cancer, and the antitumor drug is preferably cetuximab.

DETAILED DESCRIPTION OF THE INVENTION

Figure 1:
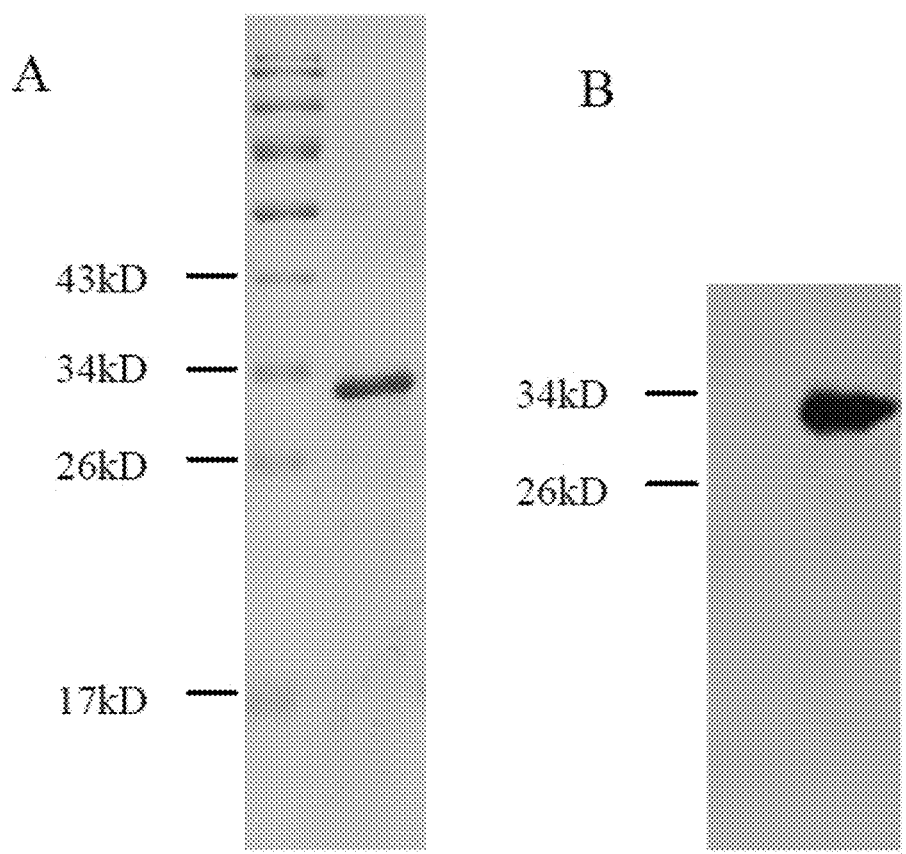
FIG. 1: Gel graph for detecting His-labeled PrPc protein with electrophoresis and antibody Western Blot method: A. electrophoretic graph; B. graph of experimental identification by western blot method with antibody 12F10.

The present invention is further illustrated with the following specific examples, but the present invention includes but is not limited to the following steps and contents.
Cell Lines and Main Reagents:

The cell lines used in the present invention included: P6C (this cell line was isolated in our laboratory from tumor tissues of colorectal cancer patient), SW480 (ATCC® CCL-228™), HCT116(ATCC® CCL-247™), MCF7 (ATCC® HTB-22™), MDA-MB-231 (ATCC® HTB-26™), HeLa, Human normal blood cell.

The main reagents used in the present invention and sources thereof were as follows:

Actin monoclonal antibody (A-5441), a-tubulin monoclonal antibody, Triton-X 100, PAGE gel preparation reagents, Tetracycline, Pipes, Digitonin purchased from Sigma;

Calreticulin monoclonal antibody purchased from Abcam;

Myc monoclonal antibody, Cytochrome C monoclonal antibody (65981A), Tim23 monoclonal antibody (611222), GM130 monoclonal antibody (610822), FITC, Cy5, Cy3 purchased from BD PharMingen;

C-myc monoclonal antibody (SC-40) purchased from Santa Cruz;

Cellulose acetate membrane used for Western blotting, Sucrose, Hepes purchased from Gibcol BRL;

Coomassie Blue G250, R250, NP-40, Tween 20, Proteinase K, DMSO purchased from Merck;

West Pico Chemiluminescent substrate, Disuccinimidyl suberate (DSS) purchased from Pierce;

X-OMAT BT Scientific Film purchased from Kodak;

PfuUltra High-Fidelity DNA Polymerases II purchased from Stratagene;

Restriction endonucleases purchased from Biolabs;

dNTP, Pyrobest DNA Polymerases purchased from Takara;

Lipofectemin2000, OPTI-MEM, MitotrackerRedC-MXROS purchased from Invitrogen;

FBS (Fetal bovine serum) purchased from Hyclone; and

Unless specifically stated, other reagents are all analytically pure reagents.

Embodiment 1. Expression and Purification of his-Labeled PrPc Protein

I. Construction of prokaryotic expression plasmids for His-labeled PrPc

1. Digestion and Recovery of pET-30a(+) Vector

Restriction enzyme cutting sites are BamH I and Xho I, dual-enzyme digestion

Enzyme-digested product was subjected to 1% agarose gel electrophoresis and recovered.

2. Acquisition, Digestion and Recovery of PrPc Full-Length Gene

PCR primer sequence:

```
SEQ ID NO: 5:
positive-sense strand:
5'-GGATCCATGGCGAACCTTGGCTG-3'

SEQ ID NO: 6:
antisense strand:
5'-CTCGAGTCCCACTATCAGGAAGA-3'

PrPc cDNA full-length sequence: SEQ ID NO: 7:
ATGGCGAACCTTGGCTGCTGGATGCTGGTTCTCTTTGTGGCCACATGG

AGTGACCTGGGCCTCTGCAAGAAGCGCCCGAAGCCTGGAGGATGGAAC

ACTGGGGGCAGCCGATACCCGGGGCAGGGCAGCCCTGGAGGCAACCGC

TACCCACCTCAGGGCGGTGGTGGCTGGGGGCAGCCTCATGGTGGTGGCT

GGGGGCAGCCTCATGGTGGTGGCTGGGGGCAGCCCCATGGTGGTGGCTG

GGGACAGCCTCATGGTGGTGGCTGGGGTCAAGGAGGTGGCACCCACAGT

CAGTGGAACAAGCCGAGTAAGCCAAAAACCAACATGAAGCACATGGCTG

GTGCTGCAGCAGCTGGGGCAGTGGTGGGGGGCCTTGGCGGCTACATGCT

GGGAAGTGCCATGAGCAGGCCCATCATACATTTCGGCAGTGACTATGAGG

ACCGTTACTATCGTGAAAACATGCACCGTTACCCCAACCAAGTGTACTAC

AGGCCCATGGATGAGTACAGCAACCAGAACAACTTTGTGCACGACTGCGT

CAATATCACAATCAAGCAGCACACGGTCACCACAACCACCAAGGGGGAG

AACTTCACCGAGACCGACGTTAAGATGATGGAGCGCGTGGTTGAGCAGAT

GTGTATCACCCAGTACGAGAGGGAATCTCAGGCCTATTACCAGAGAGGAT

CGAGCATGGTCCTCTTCTCCTCTCCACCTGTGATCCTCCTGATCTCTTTC

CTTCCTGATAGTGGGA

PrPc amino acid sequence: SEQ ID NO: 8:
MANLGCWMLVLFVATWSDLGLCKKRPKPGGWNTGGSRYPGQGSPGGN

RYPPQGGGGWGQPHGGGWGQPHGGGWGQPHGGGWGQPHGGGWGQGGGT

HSQWNKPSKPKTNMKHMAGAAAAGAVVGGLGGYMLGSAMSRPIIHFGSD

YEDRYYRENMHRYPNQVYYRPMDEYSNQNNFVHDCVNITIKQHTVTTTT

KGENFTETDVKMMERVVEQMCITQYERESQAYYQRGSSMVLFSSPPVIL

LISFVG
```

The above primer was used for PCR amplification, the product was subjected to BamH I and Xho I dual-enzyme digestion and recovery, then linkage to digested pET-30a (+) vector was performed using T4 DNA ligase.

3. Transformation and Clonal Culture in Large Scale for the Linkage Product

Top10 competent cells were taken, thawed in ice-bath; 1~5 μL of linkage product was added to the competent cells, gently agitated in ice-bath for 30 min; (attention: DNA solution volume should not exceed 10% of competent cell suspension); heat shock was performed at 42° C. for 30 s, shake was avoided during this period; then rapidly transferred to ice-bath and kept for 2 min or more; to each tube 1000 μL of LB fluid medium free of antibiotic was added, shake cultured at 37° C. and 150 rpm for 1 h to revive bacteria and express resistant gene of plasmids; centrifuged at 4000 rpm for 2 min, the supernatant was discarded, the precipitate was re-suspended with 100 μL of LB, evenly spread on kanamycin-containing LB agar plate, placed in biosafety cabinet until liquid was absorbed; placed upside down at 37° C. and cultured overnight; clones were picked and added to 1~5 mL of kanamycin-containing LB liquid culture medium for enlarge culture, after being shake suspended, the bacteria solution was taken for sequencing (or after being extracted, the obtained plasmids were taken for sequencing).

```
Sequencing result was correct: SEQ ID NO: 9:
TCATCATCATTCTTCTGGTCTGGTGCACGCTGTGAGCGGATAACAATTC

CCCTCTAGAAATAATTTTGTTTAACTTTAAGAAGGAGATATACATATGCA

CCATCATCATCATCATTCTTCTGGTCTGGTGCCACGCGGTTCTGGTATGA

AAGAAACCGCTGCTGCTAAATTCGAACGCCAGCACATGGACAGCCCAGAT

CTGGGTACCGACGACGACGACAAGGCCATGGCTGATATCGGATCCATGGC

GAACCTTGGCTGCTGGATGCTGGTTCTCTTTGTGGCCACATGGAGTGACC

TGGGCCTCTGCAAGAAGCGCCCGAAGCCTGGAGGATGGAACACTGGGGGC

AGCCGATACCCGGGGCAGGGCAGCCCTGGAGGCAACCGCTACCCACCTCA

GGGCGGTGGTGGCTGGGGGCAGCCTCATGGTGGTGGCTGGGGGCAGCCTC

ATGGTGGTGGCTGGGGGCAGCCCCATGGTGGTGGCTGGGGACAGCCTCAT

GGTGGTGGCTGGGGTCAAGGAGGTGGCACCCACAGTCAGTGGAACAAGCC

GAGTAAGCCAAAAACCAACATGAAGCACATGGCTGGTGCTGCAGCAGCTG

GGGCAGTGGTGGGGGGCCTTGGCGGCTACATGCTGGGAAGTGCCATGAGC

AGGCCCATCATACATTTCGGCAGTGACTATGAGGACCGTTACTATCGTGA

AAACATGCACCGTTACCCCAACCAAGTGTACTACAGGCCCATGGATGAGT

ACAGCAACCAGAACAACTTTGTGCACGACTGCGTCAATATCACAATCAAG

CAGCACACGGTCACCACAACCACCAAGGGGGAGAACTTCACCGAGACCGA

CGTTAAGATGATGGAGCGCGTGGTTGAGCAGATGTGTATCACCCAGTACG

AGAGGGAATCTCAGGCCTATTACCAGAGAGGATCGAGCATGGTCCTCTTC

TCCTCTCCACCTGTGATCCTCCTGATCTCTTTCCTCATCTTCCTGATAGT

GGGACTCGAGCACCACCACCACCACCACTGAGATCCGGCTGCAACAAGCA
```

PrPc gene sequence and HIS-labeled sequence were underlined.

4. Expression of Protein in Large Quantity in Rosetta Bacteria

His-labeled PrPc expression plasmid transformation of Rosetta bacteria: monoclonal bacteria containing recombinant plasmid were picked onto 5 mL of LB (containing 50 μg/mL kanamycin) and cultured overnight at 37° C. and 220 rpm; the overnight cultured bacteria was added in a ratio of 1:100 to a 2000 mL culture flask containing 500 mL of LB culture medium and cultured at 37° C. and 220 rpm until OD600 was 0.4-1.0 (most preferably 0.6), cooled to 16-20° C.; 2~5 mL of bacteria solution was taken, placed in a sterile shake bacterial tube as non-induced control group, the residual culture was added with IPTG inducer to reach a final concentration of 0.1~0.4 mM and used as experimental group, the two groups were continuously shake cultured at 16-20° C. for 16 h; 1 mL of bacterial solution was taken therefrom separately, centrifuged at 12000 g for 30 s to collect precipitate, re-suspended with 100 μL 2× protein loading buffer, mixed evenly, boiled for 10 min, the residual bacterial solution was centrifuged at 5000 rpm for 10 min, the supernatant was discarded, frozen at −80° C. for standby use; the supernatant obtained by centrifugation at 12000 g, 5 min, was used as sample for analysis such as SDS-PAGE, and Western Blot (WB) and R-250 method was used for identifying whether the protein was expressed.

5. Purification of his-Labeled Protein of Prokaryotic Expression

The bacteria as collected in step 4 were broken with ultrasound, and proteins were extracted with nickel column method under denature condition; the concentration of the collected proteins was determined by ultraviolet spectroscopy, BCA method or Coomassie brilliant blue method, and the portion containing proteins was subjected to electrophoresis to determine purity.

After expression in large scale in Rosetta bacteria, we found that almost all of the protein existed in the precipitate, so that denature condition was used for purification of protein, the used eluent had a pH of 6.0. After SDS-PAGE electrophoresis, the gel was stained with Coomassie brilliant blue R-250 to determine protein purity, and target protein was of about 34 kD, and there were few impurity bands at other positions, which showed that purification effect was good. After the specificity of protein was determined by western blot test with antibody 12F10, the result showed only one band which indicated good specificity (see FIG. 1).

Embodiment 2. Acquisition of Mouse Anti-Human PrPc Antibody

1. Immunization of Animals

The purified His-PrPc protein was taken, subcutaneously primarily immunized specific-pathogen-free (SPF) grade Balb/c female mice, No. 1, 2 and 3; the immunizing dose was 60 μg of protein/mouse. After two weeks, the first booster immunization was performed subcutaneously, and the immunizing dose was 30 μg of protein/mouse. After another two weeks, the second booster immunization was performed, and the immunizing dose was 30 μg of protein/mouse. After further two weeks, the third booster immunization was performed subcutaneously, and the immunizing dose was 30 μg of protein/mouse. After one week, blood sample was taken from eye socket for determine antiserum titer.

2. Titer Determination

Steps: 2 μg/mL, coated at 4° C. overnight; 1% BSA, blocked at 37° C. for 2 h; antiserum was double diluted from a 200-fold dilution, the blank control (blank) was PBS, the negative control (negative) was negative serum diluted by 200 folds.

3. Cell Fusion Test

Mouse spleen cells and SP2/0 cells were taken, fused by PEG method. The fused cells were selected and cultured with semi-solid culture medium (containing HAT).

4. Picking Clones

5×93 cell monoclones were picked out, cultured on 5 96-well cell culture plates (the plates were coated with thymocyte cells in advance, 100 μL/well);

5. First Screening of Monoclonal Cells

The plates were coated with immunogen, the selected clones were subjected to first screening by ELISA method.

6. Second Screening of Monoclonal Cells

ELISA antigen was used to coat other proteins which had antigen as immunogen and had his-tag;

Experimental steps were the same for the first screening, and 20 positive hybridoma cell strains were obtained.

7. Identification of Monoclonal Cell Subclass

The 20 positive cell strains obtained via the second screening were subjected to subclass identification, and 16 positive antibody strains were finally obtained (15 IgG strains, 1 IgA strain).

8. Cryopreservation

Preparation of cryopreservation solution, FBS:IMDM:DMSO (volume ratio)=7:2:1;

3 Tubes of each strain were cryopreserved, and another 3 tubes were cryopreserved after 3 days, in which cryopreservation was performed by cryopreservation box method at −80° C. overnight, then moved to preserved in liquid nitrogen tank.

For those cell lines with stronger antibody secretory capacity, RNA extraction inverse transcription and antibody variable region PCR amplification and sequencing were carried out, and we obtained anti-PrPc mAb-3, anti-PrPc mAb-5, anti-PrPc mAb-25, in which the variable region of anti-PrPc mAb-5 had cDNA sequence as follows:

PrPc Ab-5 VH:
SEQ ID NO: 4
1-CACCATGGAATGCAGCTGGGTCATCCTCTTTCTCTTGTCAGGAACTG

GAGGTGTCCTCTCTGAGGTCCAACTGCAACAGTCTGGACCTGAGCTGGTG

AAGCCTGGGGCTTCAGTGAAGATGTCCTGCAAGGCTTCTGGATACACCTT

CACTGACTACTACATGAAGTGGGTGAAGCAGAGCCATGGAAAGAGCCTTG

AGTGGATTGGAGATATTAATCCTAACAATGGTGATACTTTCTACAACCAG

AAGTTCAAGGGCAAGGCCACATTGACTGTTGACAAATCCTCCAACACAGC

CTACATGCAGCTCAACAGCCTGACATCTGAGGACTCTGCAGTCTATTACT

GTGCAAAACCTGGGCGGACTTACTGGGGCCAAGGGACTCTGGTCACTGTC

TCTGCAGCCAAAACAACAGCCCCATCGGTCTATCCACTGGCCCCTGTGTG

TGGAGGTTCTAGACCT-463

PrPc Ab-5 VL:
SEQ ID NO: 3
1-CACCATGGAGACAGACACACTCCTGCTATGGGTACTGCTGCTCTGGG

TTCCAGGTTCCACTGGTGACATTGTGCTGACACAGTCTCCTGCTTCCTTA

GCTGTATCTCTGGGGCAGAGGGCCACCATCTCATACAGGGCCAGCAAAAG

TGTCAGTACATCTGGCTATAGTTATATGCACTGGAACCAACAGAAACCAG

GACAGCCACCCAGACTCCTCATCTATCTTGTATCCAACCTAGAATCTGGG

GTCCCTGCCAGGTTCAGTGGCAGTGGGTCTGGGACAGACTTCACCCTCAA

CATCCATCCTGTGGAGGAGGAGGATGCTGCAACCTATTACTGTCAGCACA

TTAGGGAGCTTACACGTTCGGAGGGGGGACCAAGCTGGAAA-447

Corresponding amino acid sequence are as follows:

PrPc Ab-5 VH:
SEQ ID NO: 2
MECSWVILFLLSGTGGVLSEVQLQQSGPELVKPGASVKMSCKASGYTFT
DYYMKWVKQSHGKSLEWIGDINPNNGDTFYNQKFKGKATLTVDKSSNTAY
MQLNSLTSEDSAVYYCAKPGRTYWGQGTLVTVSAAKTTAPSVYPLAPVCG
GSRP

PrPc Ab-L5 VL:
SEQ ID NO: 1
TMETDTLLLWVLLLWVPGSTGDIVLTQSPASLAVSLGQRATISYRASKSV
STSGYSYMHWNQQKPGQPPRLLIYLVSNLESGVPARFSGSGSGTDFTLNI
HPVEEEDAATYYCQHIRELTRSEGGPSWK

Embodiment 3. Determination of Antigen-Binding Epitopes of Ab-3, 5, 25, 12F10 for PrPc 1. Construction of Truncated Expression Plasmids for PrPc Wildtype (wt) was constructed already in our laboratory (obtained by construction via cloning a PrPc wild-type gene complete sequence into plasmid pCDNA4.0TO/MY-C.HIS.B), for different truncated expression plasmids, the above mutant primers were used and wt plasmid was used as template, PCR reaction was performed with pyrobest high fidelity enzyme, the PCR product was identified with 1% agarose electrophoresis, digested with DpnI, to remove originally contained methylated double-stranded DNA template, then used for transformation of bacteria (*E. coli* competent Top10), and confirmed by sequencing. If the result was correct, the truncated expression plasmids for PrPc were obtained. After sequencing successfully, enlarge culture could be performed according to experimental requirement, and a large amount of plasmids could be extracted for standby use.

The used plasmid: pCDNA4.0TO/myc.HIS.B, cleavage sites: Kpn I and Xho I

WT primers:

SEQ ID NO: 10: wtPrP$^c$ F:
5'-GG GGTACC ATGGCGAACCTTGGCTGC-3'

SEQ ID NO: 11: wtPrP$^c$ R:
5'-CCG CTCGAG CC TCCCACTATCAGGAAGATGA-3' wt relative molecular weight: ~34 k (8 k tag)

2. Mutant types were designed according to PrPc functional region and amino acid sequence information, and the designed mutant sequence structures and truncated mutant primers were as follows:

(1) PrPc-1: N-signal peptide (1-50)
Base: SEQ ID NO: 12:
ATGGCGAACCTTGGCTGCTGGATGCTGGTTCTCTTTGTGGCCACATGG
AGTGACCTGGGCCTCTGCAAGAAGCGCCCGAAGCCTGGAGGATGGAACAC
TGGGGGCAGCCGATACCCGGGGCAGGGCAGCCCTGGAGGCAACCGCTACC
CA

AA: SEQ ID NO: 13:
MANLGCWMLVLFVATWSDLGLCKKRPKPGGWNTGGSRYPGQGSPGGN
RYP

Truncated Mutant Primers:

SEQ ID NO: 14: PrP$^c$-1F:
5'-GGCAACCGCTACCCAGGACGAGCTCAGATCTCCCGGGCGC-3'

SEQ ID NO: 15: mPrP$^c$-1R:
5'-CTAGACTCGAGCTCCTGGGTAGCGGTTGCCTCCAGGGCTG-3'

(2) PrPc-2: five octapeptide repeats - C terminal (51-253)
Base: SEQ ID NO: 16:
CCTCAGGGCGGTGGTGGCTGGGGCAGCCTCATGGTGGTGGCTGGGG
GCAGCCTCATGGTGGTGGCTGGGGGCAGCCCCATGGTGGTGGCTGGGGAC
AGCCTCATGGTGGTGGCTGGGGTCAAGGAGGTGGCACCCACAGTCAGTGG
AACAAGCCGAGTAAGCCAAAAACCAACATGAAGCACATGGCTGGTGCTGC
AGCAGCTGGGGCAGTGGTGGGGGGCCTTGGCGGCTACATGCTGGGAAGTG
CCATGAGCAGGCCCATCATACATTTCGGCAGTGACTATGAGGACCGTTAC
TATCGTGAAAACATGCACCGTTACCCCAACCAAGTGTACTACAGGCCCAT
GGATGAGTACAGCAACCAGAACAACTTTGTGCACGACTGCGTCAATATCA
CAATCAAGCAGCACACGGTCACCACAACCACCAAGGGGGAGAACTTCACC
GAGACCGACGTTAAGATGATGGAGCGCGTGGTTGAGCAGATGTGTATCAC
CCAGTACGAGAGGGAATCTCAGGCCTATTACCAGAGAGGATCGAGCATGG
TCCTCTTCTCCTCTCCACCTGTGATCCTCCTGATCTCTTTCCTCATCTTC
CTGATAGTGGGA AA: SEQ ID NO: 17:
PQGGGGWGQPHGGGWGQPHGGGWGQPHGGWGQPHGGGWGQGGGT
HSQWNKPSKPKTNMKHMAGAAAAGAVVGGLGGYMLGSAMSRPIIHFGSDY
EDRYYRENMHRYPNQVYYRPMDEYSNQNNFVHDCVNITIKQHTVTTTTKG
ENFTETDVKMMERVVEQMCITQYERESQAYYQRGSSMVLFSSPPVILLIS
FLIFLIVG Truncated Mutant Primers:

SEQ ID NO: 18: PrP$^c$-2F:
5'-AAGCTTGGTACCATGCCTCAGGGCGGTGGTGGCTGGGGGC-3'

SEQ ID NO: 19: PrP$^c$-2R:
5'-ACCACCGCCCTGAGGCATGGTACCAAGCTTAACTAGCCAG-3'

(3) PrPc-3: hydrophobic domain - C terminal (106-253)
Base: SEQ ID NO: 20:
AAAACCAACATGAAGCACATGGCTGGTGCTGCAGCAGCTGGGGCAGT
GGTGGGGGGCCTTGGCGGCTACATGCTGGGAAGTGCCATGAGCAGGCCCA
TCATACATTTCGGCAGTGACTATGAGGACCGTTACTATCGTGAAAACATG
CACCGTTACCCCAACCAAGTGTACTACAGGCCCATGGATGAGTACAGCAA
CCAGAACAACTTTGTGCACGACTGCGTCAATATCACAATCAAGCAGCACA
CGGTCACCACAACCACCAAGGGGGAGAACTTCACCGAGACCGACGTTAAG
ATGATGGAGCGCGTGGTTGAGCAGATGTGTATCACCCAGTACGAGAGGGA -continued
ATCTCAGGCCTATTACCAGAGAGGATCGAGCATGGTCCTCTTCTCCTCTC

CACCTGTGATCCTCCTGATCTCTTTCCTCATCTTCCTGATAGTGGGA

AA: SEQ ID NO: 21:
KTNMKHMAGAAAAGAVVGGLGGYMLGSAMSRPIIHFGSDYEDRYYRE

NMHRYPNQVYYRPMDEYSNQNNFVHDCVNITIKQHTVTTTTKGENFTETD

VKMMERVVEQMCITQYERESQAYYQRGSSMVLFSSPPVILLISFLIFLIV

G

Truncated Mutant Primers:

SEQ ID NO: 22: PrP$^c$-3F:
5'-AAGCTTGGTACCATGAAAACCAACATGAAGCACATGGCTG-3'

SEQ ID NO: 23: PrP$^c$-3R:
5'-CTTCATGTTGGTTTTCATGGTACCAAGCTTAACTAGCCAG-3'

(4) PrPc-4: β1 - C terminal (127-253)
Base: SEQ ID NO: 24:
GGCTACATGCTGGGAAGTGCCATGAGCAGGCCCATCATACATTTCGGC

AGTGACTATGAGGACCGTTACTATCGTGAAAACATGCACCGTTACCCCAA

CCAAGTGTACTACAGGCCCATGGATGAGTACAGCAACCAGAACAACTTTG

TGCACGACTGCGTCAATATCACAATCAAGCAGCACACGGTCACCACAACC

ACCAAGGGGAGAACTTCACCGAGACCGACGTTAAGATGATGGAGCGCGT

GGTTGAGCAGATGTGTATCACCCAGTACGAGAGGGAATCTCAGGCCTATT

ACCAGAGAGGATCGAGCATGGTCCTCTTCTCCTCTCCACCTGTGATCCTC

CTGATCTCTTTCCTCATCTTCCTGATAGTGGGA

AA: SEQ ID NO: 25:
GYMLGSAMSRPIIHFGSDYEDRYYRENMHRYPNQVYYRPMDEYSNQNN

FVHDCVNITIKQHTVTTTTKGENFTETDVKMMERVVEQMCITQYERESQA

YYQRGSSMVLFSSPPVILLISFLIFLIVG

Truncated Mutant Primers:

SEQ ID NO: 26: PrP$^c$-4F:
5'-AAGCTTGGTACCATGGGCTACATGCTGGGAAGTGCCATGA-3'

SEQ ID NO: 27: PrP$^c$-4R: 5'-TCCCAGCATGTAGCC
CATGGTACCAAGCTTAACTAGCCAG-3'

(5) PrPc-5: α1 - C terminal (144-253)
Base: SEQ ID NO: 28:
GACTATGAGGACCGTTACTATCGTGAAAACATGCACCGTTACCCCAAC

CAAGTGTACTACAGGCCCATGGATGAGTACAGCAACCAGAACAACTTTGT

GCACGACTGCGTCAATATCACAATCAAGCAGCACACGGTCACCACAACCA

CCAAGGGGAGAACTTCACCGAGACCGACGTTAAGATGATGGAGCGCGTG

GTTGAGCAGATGTGTATCACCCAGTACGAGAGGGAATCTCAGGCCTATTA

CCAGAGAGGATCGAGCATGGTCCTCTTCTCCTCTCCACCTGTGATCCTCC

TGATCTCTTTCCTCATCTTCCTGATAGTGGGA

AA: SEQ ID NO: 29:
DYEDRYYRENMHRYPNQVYYRPMDEYSNQNNFVHDCVNITIKQHTVTT

TTKGENFTETDVKMMERVVEQMCITQYERESQAYYQRGSSMVLFSSPPVI

LLISFLIFLIVG

Truncated Mutant Primers:

SEQ ID NO: 30: PrP$^c$-5F:
5'-AAGCTTGGTACCATGGACTATGAGGACCGTTACTATCGTG-3'

SEQ ID NO: 31: PrP$^c$-5R:
5'-ACGGTCCTCATAGTCCATGGTACCAAGCTTAACTAGCCAG-3'

(6) PrPc-6: β2 - C terminal (162-253)
Base: SEQ ID NO: 32:
CAAGTGTACTACAGGCCCATGGATGAGTACAGCAACCAGAACAACTTT

GTGCACGACTGCGTCAATATCACAATCAAGCAGCACACGGTCACCACAAC

CACCAAGGGGAGAACTTCACCGAGACCGACGTTAAGATGATGGAGCGCG

TGGTTGAGCAGATGTGTATCACCCAGTACGAGAGGGAATCTCAGGCCTAT

TACCAGAGAGGATCGAGCATGGTCCTCTTCTCCTCTCCACCTGTGATCCT

CCTGATCTCTTTCCTCATCTTCCTGATAGTGGGA

AA: SEQ ID NO: 33:
QVYYRPMDEYSNQNNFVHDCVNITIKQHTVTTTTKGENFTETDVKMMER

VVEQMCITQYERESQAYYQRGSSMVLFSSPPVILLISFLIFLIVG

Truncated Mutant Primers:

SEQ ID NO: 34: PrP$^c$-6F:
5'-AAGCTTGGTACCATGCAAGTGTACTACAGGCCCATGGATG-3'

SEQ ID NO: 35: PrP$^c$-6R:
5'-CCTGTAGTACACTTGCATGGTACCAAGCTTAACTAGCCAG-3'

(7) PrPc-7: α2 - C terminal (173-253)
Base: SEQ ID NO: 36:
CAGAACAACTTTGTGCACGACTGCGTCAATATCACAATCAAGCAGCAC

ACGGTCACCACAACCACCAAGGGGAGAACTTCACCGAGACCGACGTTAA

GATGATGGAGCGCGTGGTTGAGCAGATGTGTATCACCCAGTACGAGAGGG

AATCTCAGGCCTATTACCAGAGAGGATCGAGCATGGTCCTCTTCTCCTCT

CCACCTGTGATCCTCCTGATCTCTTTCCTCATCTTCCTGATAGTGGGA

AA: SEQ ID NO: 37:
QNNFVHDCVNITIKQHTVTTTTKGENFTETDVKMMERVVEQMCITQYER

ESQAYYQRGSSMVLFSSPPVILLISFLIFLIVG

Truncated Mutant Primers:

SEQ ID NO: 38: PrP$^c$-7F:
5'-AAGCTTGGTACCATGCAGAACAACTTTGTGCACGACTGCG-3'

SEQ ID NO. 39: PrP$^c$-7R:
5'-CACAAAGTTGTTCTGCATGGTACCAAGCTTAACTAGCCAG-3'

(8) PrPc-8: α3 - C terminal (195-253)
Base: SEQ ID NO: 40:
GGGGAGAACTTCACCGAGACCGACGTTAAGATGATGGAGCGCGTGGT

TGAGCAGATGTGTATCACCCAGTACGAGAGGGAATCTCAGGCCTATTACC

AGAGAGGATCGAGCATGGTCCTCTTCTCCTCTCCACCTGTGATCCTCCTG

ATCTCTTTCCTCATCTTCCTGATAGTGGGA

AA: SEQ ID NO: 41:
GENFTETDVKMMERVVEQMCITQYERESQAYYQRGSSMVLFSSPPVILLI

SFLIFLIVG

Truncated Mutant Primers:

SEQ ID NO: 42: PrP$^c$-8F:
5'-AAGCTTGGTACCATGGGGGAGAACTTCACCGAGACCGACG-3'

SEQ ID NO: 43: PrP$^c$-8R:
5'-GGTGAAGTTCTCCCCCATGGTACCAAGCTTAACTAGCCAG-3'

(9) PrPc-9: C-ancre peptide (231-253)
Base: SEQ ID NO: 44:
AGCATGGTCCTCTTCTCCTCTCCACCTGTGATCCTCCTGATCTCTTTCCT

CATCTTCCTGATAGTGGGA

AA: SEQ ID NO: 45:
SMVLFSSPPVILLISFLIFLIVG

Truncated Mutant Primers:

SEQ ID NO: 46:
PrP$^c$-9F:
5'-AAGCTTGGTACCATGAGCATGGTCCTCTTCTCCTCTCCAC-3'

SEQ ID NO: 47:
PrP$^c$-9R:
5'-GAAGAGGACCATGCTCATGGTACCAAGCTTAACTAGCCAG-3'

Figure 2:
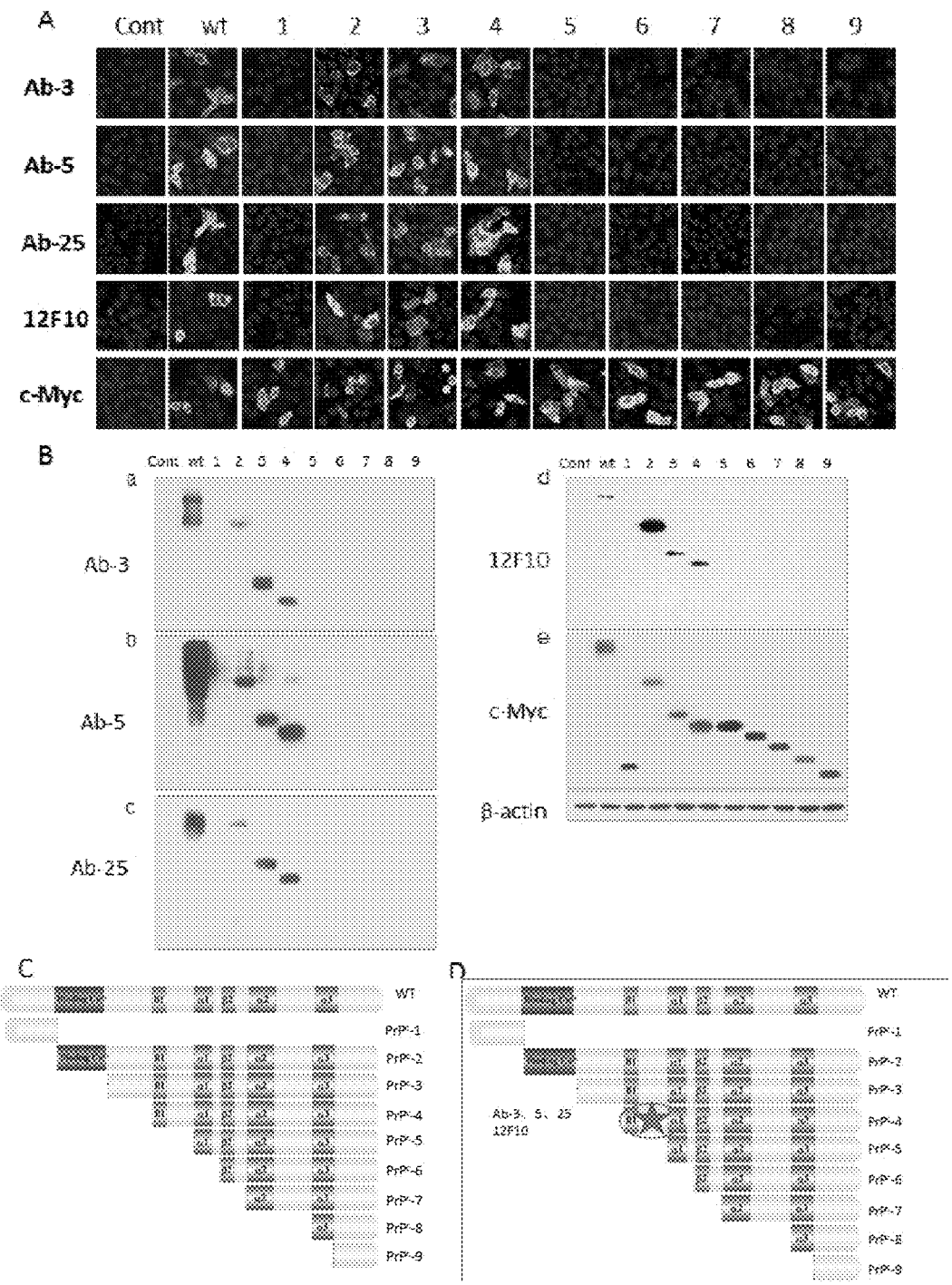
FIG. 2: Diagrams of antigen-binding epitopes of Ab-3, 5, 25 and 12F10 for PrPc: A. detection of various antibodies binding to 9 kinds of PrPc by cell immunofluorescence method; B. detection of various antibodies binding to 9 kinds of PrPc by Western Blotting method; C. schematic diagrams for 9 kinds of PrPc mutants; D. schematic diagram of localization of antibody-binding region.

As stated above, we constructed 9 PrPc mutants (FIG. 2C), liposome-mediated transfection method was used to transfect Hela cells, cellular immunofluorescence method and western blotting method were used to verify interaction relation between PrPc protein mutants and Ab-3, 5, 25 as well as commercial antibody 12F10 antibody, and the epitopes for interaction between these antibodies and PrPc protein were determined according to the experimental results. The two kinds of antibody had antigen-binding epitopes to PrPc at the same positions, and they bound to PrPc mutants as far as to mutant 4 (FIGS. 2A and B), but did not bind to mutant 5 and subsequent mutants, which showed that their binding sites located in β1α1 region (FIG. 2D), and in this region, AA site was from 127 to 161, including 35 amino acids in total, and its sequence structure was:
SEQ ID NO:48: GYMLGSAMSRPIIHFGSDYE-DRYYRENMHRYPNQV.

Figure 3:
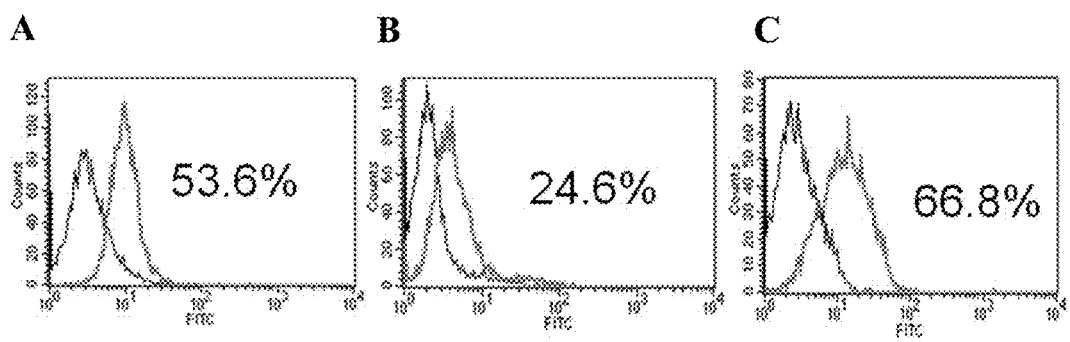
FIG. 3: Expression statuses of PrPc in different cell lines: A. P6C cell; B. SW480 cell; C. HCT116 cell.

Embodiment 4. PrPc Antibody Showed Significant Ability in Inhibition of Migration of PrPc-Positive Colorectal Cancer Cell Line The verified PrPc antibody Ab-3 was used as primary antibody to identify PrPc expression in different colorectal cancer cell lines (P6C, SW480 and HCT116) as well as breast cancer cell line (MCF7) (the culture medium for the aforementioned cells was HDMEM containing 10% FBS) PrPc, Flow cytometer was used to analyze these cell lines, and the results showed different expression rates in all of these cell lines, in which P6C, SW480 and HCT116 separately were 53.6%, 24.6% & 66.8% (FIG. 3), so that these 3 cell lines could be used in research of relation between PrPc antibody and tumor therapy, while MCF7 could be used as negative control.

Cell migration transwell technique was used to determine changes of migration ability after antibody treatment of PrPc-positive cells. Specific steps of Transwell counting method were as follows: cells were digested, after end of digestion, centrifuged and culture medium was discarded, PBS was used for washing twice, serum-free culture medium was used for re-suspension. Cell density was adjusted to $1\times10^6$, 100 μl ($1\times10^5$) of cell suspension was added with PrPc antibody in different concentrations, evenly mixed and added to Transwell chamber with pore diameter of 8 μm matched with a 24-well plate; the lower layer was culture media containing 10% FBS and PrPc antibody in different concentrations, 600 μL/well, after conventional culture for 24 h, the cells were fixed, stained with R-250, observed under microscope, photographed, and counted, and cell numbers passing through pores were subjected to statistics.

The used antibody concentration was 10 μg/mL, the treatment time was 24 h, and the results showed that in comparison with IgG control group, all experimental groups added with PrPc antibody showed significant inhibition in cell migration ability according to observation under optical microscope. The cells passing through transwell chamber membrane were counted under the same one field of view and a mean number of cells was obtained, so that the inhibition rates of cell migration for antibodies could be obtained via statistics, in which results of inhibition rates for Ab-5 antibody with best inhibition effects in cell migration were shown in Table 1.

TABLE 1

Effects of Ab-5 antibody in inhibition of migration of PrPc-positive colorectal cancer cells

| | Cell | | |
|---|---|---|---|
| Antibody | IgG negative control Migrated cell number/ Inhibition rate | Ab-5 antibody Migrated cell number/ Inhibition rate | 12F10 positive control Migrated cell number/ Inhibition rate |
| P6C | 780/0% | 209/73.2% | 339/56.5% |
| SW480 | 202/0% | 111/44.8% | 145/28.1% |
| HCT116 | 365/0% | 192/47.5% | 269/26.4% |
| MDA-MB-231 | 1050/0% | 695/33.8% | 801/23.7% |

Embodiment 5. PrPc Antibody Showed No Significant Effect on Cancer Cell Viability, Ab-5 Showed an Affinity to Antigen Stronger than Those of Ab-3, 25 and 12F10

Figure 4:
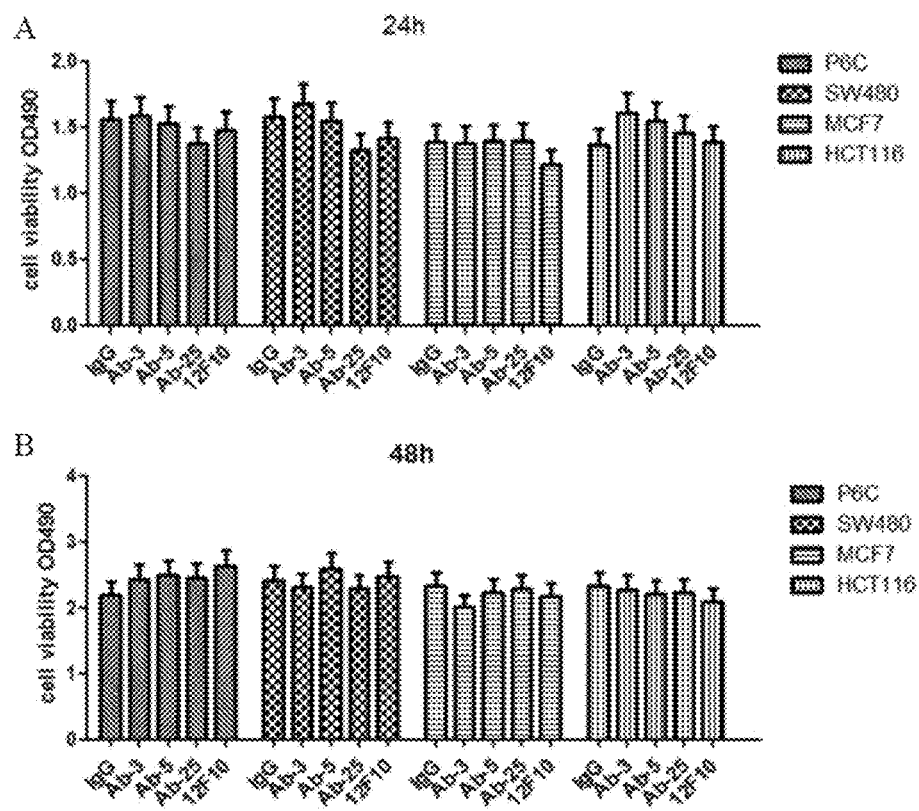
FIG. 4: Effects of antibody on viability of different cells: A. treatment time 24 h; B. treatment time 48 h.

After the cells were treated for 24 h and 48 h by adding antibody, cell viability data were determined by MTT method, and data analysis showed that in comparison with IgG control group, PrPc positive or non-positive cancer cells treated with PrPc antibody for 24 h (FIG. 4A) and 48 h (FIG. 4B) exhibited no significant change in cell viability which suggested that the PrPc antibody had no influence on cell viability.

According to binding epitopes of antibody for PrPc, the length of PrPc protein was shortened as much as possible so that the expressed protein was soluble. By using Biacore experiment, we designed mutant with GST label, GST-PrPc (β1α1), its total protein molecular weight combined with GST was about 32 kD. After expression and purification, we obtained GST-PrPc (β1α1) protein with good solubility and high purity.

Figure 5:
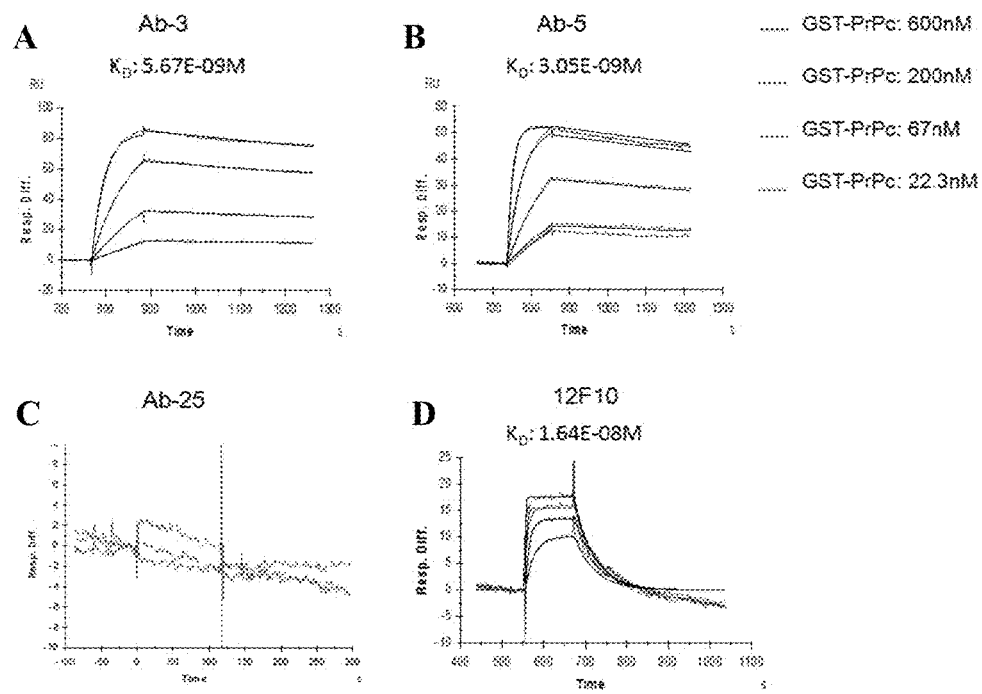
FIG. 5: Affinity and dissociation dynamic curves of different antibodies to antigen: A. Ab-3 antibody; B. Ab-5 antibody; C. Ab-25 antibody; D. 12F10 antibody.

By using Biacore experiment, kinetic constants of affinity and dissociation between Ab-3, 5, 25 as well as 12F10 and soluble GST-PrPc (β1α1) protein were determined, and affinity values between each other were calculated. The results showed that under different antigen concentrations, such as 600 μM, 200 μM, 67 μM, 22.3 μM, 7.4 μM, Ab-3, 5, 25 and 12F10 showed different affinities to antigen, in which Ab-25 had the lowest affinity, and its kinetic constant to antigen could not be well detected, while Ab-3, 5 and 12F10 showed good affinity and dissociation kinetic curves (FIG. 5), and the calculation results showed the affinities of these 3 antibodies to antigen were separately 5.67E-09M, 3.05E-09M and 1.64E-08M. Ab-5 showed affinity to antigen 1.87 times that of Ab-3, and 5.38 times that of 12F10, and thus got the highest affinity.

Figure 6:
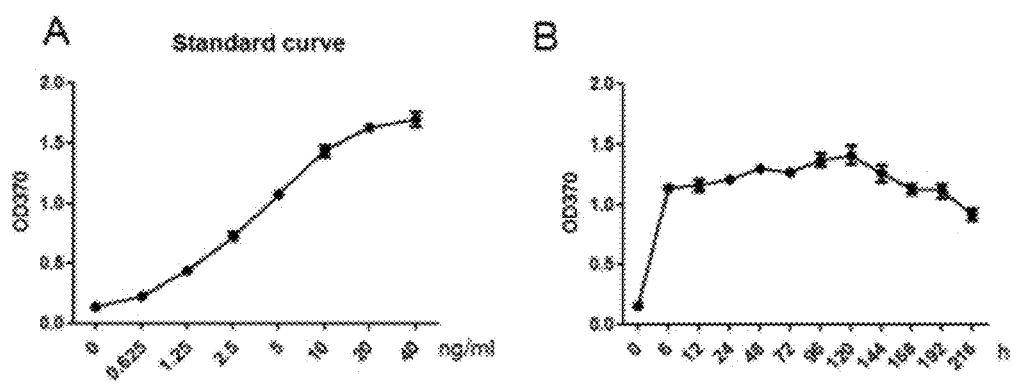
FIG. 6: Metabolism curve of Ab-5 antibody in mice body: A. standard curve of antibody concentration versus injection concentration; B. antibody concentration versus time.

Embodiment 6. PrPc Antibody could Maintain a Relatively High In Vivo Concentration for a Long Time in Mice Ab-5 antibody (concentration: 2 mg/mL) was injected into abdominal cavity of NOD/SCID mice in an amount of 100 µg of antibody per 10 g of bodyweight, and blood samples were collected separately from mouse tails after 6 h, 12 h, 24 h, 48 h, 72 h, 96 h, d 5, d 6, d 7, d 8, d 9, diluted in 1:1000, subjected to ELISA test, and according to standard curve analysis (FIG. 6), the antibody concentration in blood of mouse could reach a relatively high level after 6 h, corresponding concentration was about 5.8 µg/mL, and this concentration could be maintained for 144 hours, then started to decrease. During the period of our detection, the antibody concentration after 216 h (the $9^{th}$ day) was still 80.4% of that after 6 h, and still did not reach the half-life period (FIG. 6).

Embodiment 7. PrPc Antibody Had Good Therapeutic Effects on Cecal Tumor in Mice After 6 weeks that wildtype C57 mice were intraperitoneally injected with IgG and Ab-5, the mice were weighed, dissected, observed in main visceral organs such as liver, and there was no significant difference between two groups, and livers showed no significant difference in color and size, and average bodyweights of mice were substantially the same, i.e., about 29 g, showing no obvious difference. The results showed that the antibody of the present invention had low toxicity for normal mice, and had good biological safety.

$2\times10^6$ DeRed-P6C cells were inoculated in situ at cecum of NOD/SCID mice, the DeRed-P6C cells with fluorescence-labeling gene were prepared by a method comprising: inoculating P6C cells on 6-well plate, when cells growing to 80-90% confluence, transfecting with pDsRed2-N1 wildtype plasmid by using lipofectemin2000 kit, changing medium solution after 5 h (HDMEM containing 10% FBS), conventionally culturing for 24 h, digesting cells to form a suspension of single cells, screening DeRed positive cells by using flow cytometer with exciting light of 556 nm and emitting light of 586 nm, then the DsRed positive cells were amplified and cultured, the screening was performed for 10 times or more, and when the rate of DsRed positive cells was stabled at 95% or more, DsRed-P6C stable cell line was obtained. After inoculation for 3 weeks, small animal living imaging technique was used to observe whether tumors were inoculated successfully, and the results showed that most tumors were inoculated successfully. Then, the mice were grouped for antibody treatment experiment (FIG. 7A, the mice of the first row), there were 4 groups in the experiment, i.e., IgG control group, Ab-3 experimental group, Ab-5 experimental group and Ab-25 experimental group.

Figure 7:
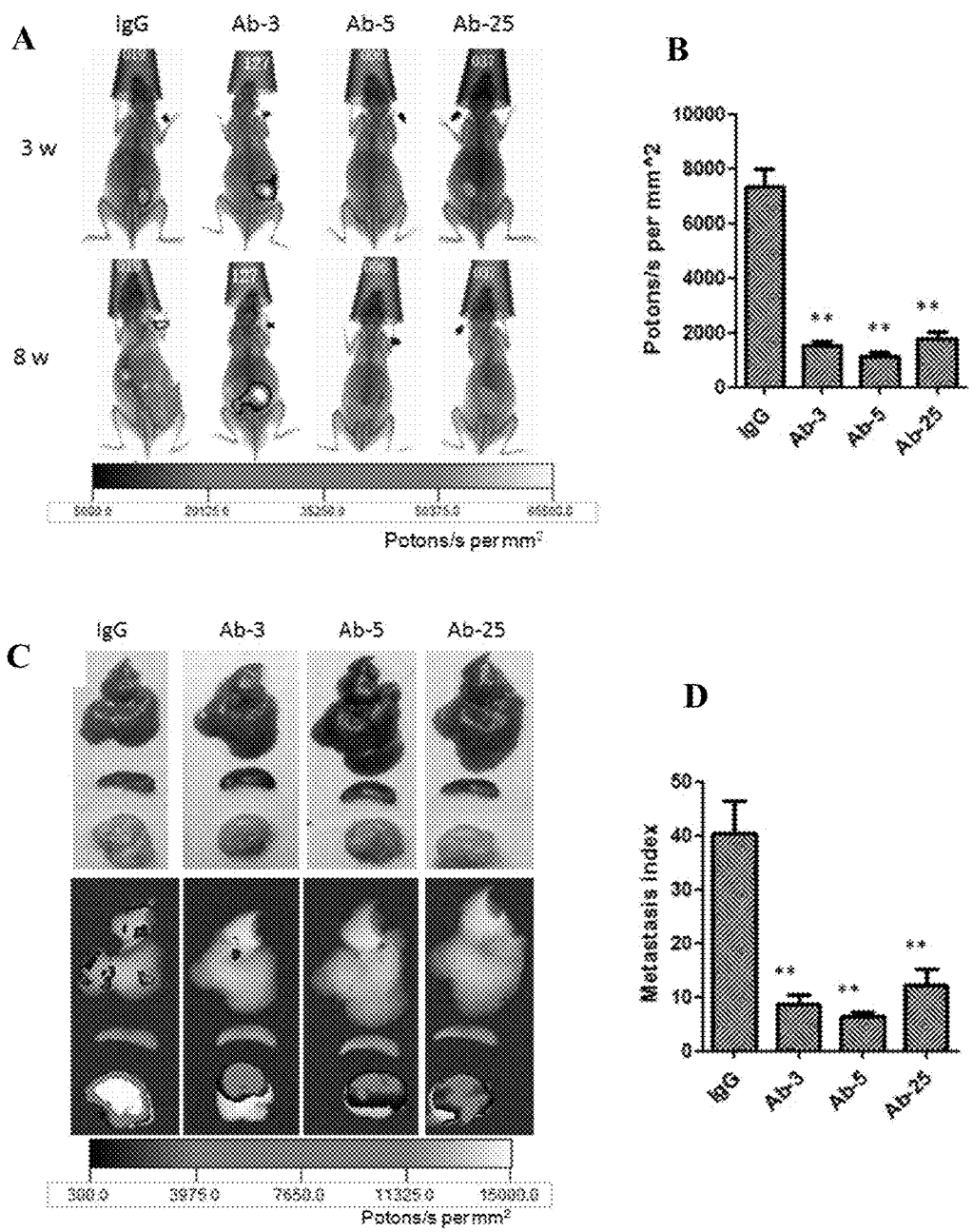
FIG. 7: Therapeutic effects of Ab-5 antibody on tumor-bearing mice: A. fluorescence imaging of living tumor cells; B. size of tumor in situ; C. anatomic atlas of different internal organs and tumor fluorescence signal localization; D. tumor cell transfer index.

After consecutive administration for 5 weeks, i.e., in the $8^{th}$ week of tumor inoculation, the mice of IgG control group showed obvious abdominal dropsy, which was caused by volume increase of tumor in situ and liver metastasis, on the contrary, the mice of administration groups showed no abdominal enlargement, i.e., there was no obvious abdominal dropsy (FIG. 5A, the mice of the second row), the living imaging data also showed that the antibody treatment groups had obviously smaller fluorescence signals in abdominal cavity in comparison with the control group, and the differences of their data were significant, in which Ab-5 treatment group had the smallest fluorescence signals (FIG. 7B). By anatomical observation and fluorescence imaging data of isolated organs, we found that the mice of antibody treatment group had little or no ascetic fluid, the tumor in situ had small volume, and there were less liver tumor lesions; while the mice of IgG control group had a lot of ascetic fluid in abdomen, the tumor in situ had large volume, and there were many liver tumor lesions (FIG. 7C). The number of liver tumor metastasis lesions was obtained via stereoscope observation, and it was divided by the mass of tumor in situ to obtain a tumor metastasis index for each group. The analysis results showed that the tumor metastasis index of the PrPc antibody treatment group was significantly lower than that of the IgG control group, and the difference in data was very obvious. In addition, among the three PrPc antibody groups, the Ab-5 treatment group had the lowest tumor metastasis index, which indicated that the Ab-5 had better tumor therapeutic effects (FIG. 7D).

Figure 8:
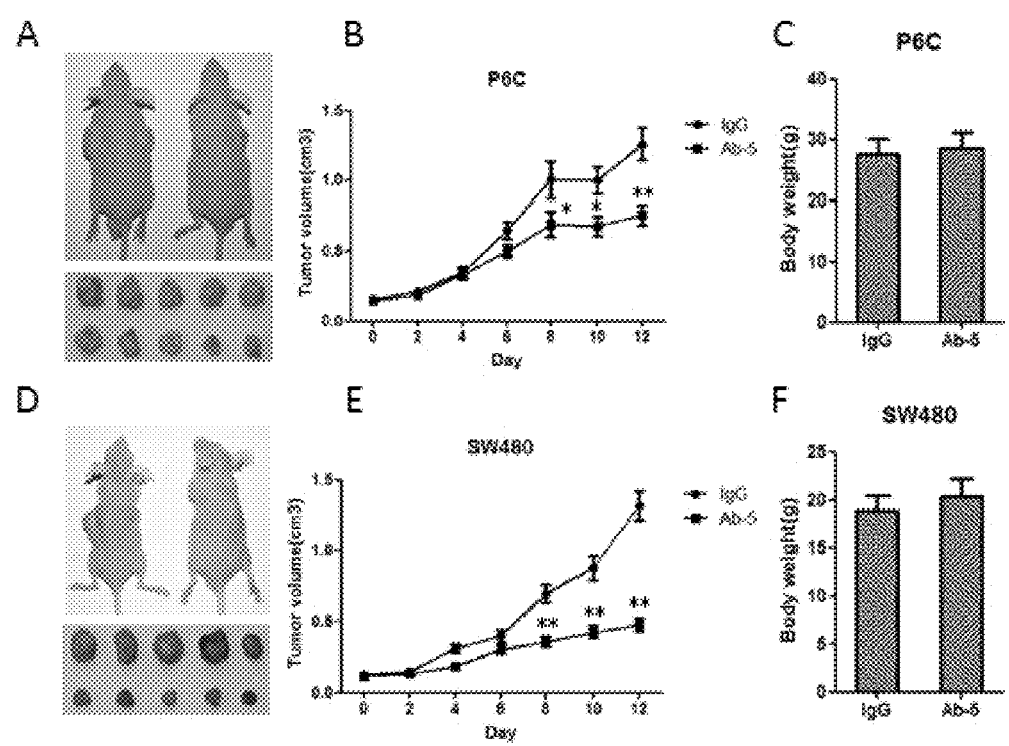
FIG. 8: Ab-5 antibody could effectively inhibit growth of subcutaneous tumor in nude mice: A to B. sizes of P6C tumors in situ of treatment group and control group; C. bodyweights of mice of treatment group and control group; D to E. sizes of SW480 tumors in situ in treatment group and control group; F. bodyweights of mice of treatment group and control group.

$2\times10^6$ Tumor cells (P6C and SW480 cells, each kind of cells were further divided into two groups, i.e., IgG control group and Ab-5 treatment group, 10 mice per group) were inoculated subcutaneously at each of right and left backsides of fore limbs of nude mice, tumors became evident after about 10 days (~0.3 mm in diameter), intraperitoneal injection of antibody started for treatment (10 mg/kg bodyweight, twice injection per week), form the same day of injecting antibody (d0), tumor sizes and bodyweights were measured every second day, tumor sizes were calculated according to formula, and volume growth curves were made. The mice were dissected after two weeks (a number of mice were remained for observing survivorship curve), subcutaneous tumors were obtained, after photographing, the tumors were fixed and preserved for downstream experiments. Through consecutive measurement of tumor sizes, we found that in the P6C models, the tumor volume of the Ab-5 treatment group was significantly different from that of the IgG control group after the $8^{th}$ day, and more different on the $12^{th}$ day, the tumor volume of the former was about 60% of that of the control group, but the bodyweights of the two groups showed no significant difference (FIG. 8A, B, C); similarly, in the SW480 models, the tumor volume of the Ab-5 treatment group was significantly different from that of the IgG control group after the $8^{th}$ day, and more different on the $12^{th}$ day, the tumor volume of the former was about 36.2% of that of the control group, the final bodyweight of IgG group was about 1.5 g less than that of the Ab-5 group, but there was no significant difference in statistics (FIG. 8D, E, F).

Embodiment 8. Ab-5 and Cetuximab Combined Treatment could Better Inhibit Growth and Metastasis of Tumor In Situ There were 7 groups of experimental animals for combined treatment: 1) IgG Cont 10 mg/kg, 2) PrPc Ab-5 10 mg/kg, 3) Cetuximab 10 mg/kg, 4) combination: PrPc Ab-5+cetuximab 10 mg/kg each, 5) PrPc Ab-5 40 mg/kg, 6) Cetuximab 40 mg/kg, 7) combination: PrPc Ab-5+cetuximab 40 mg/kg each.

Figure 9:
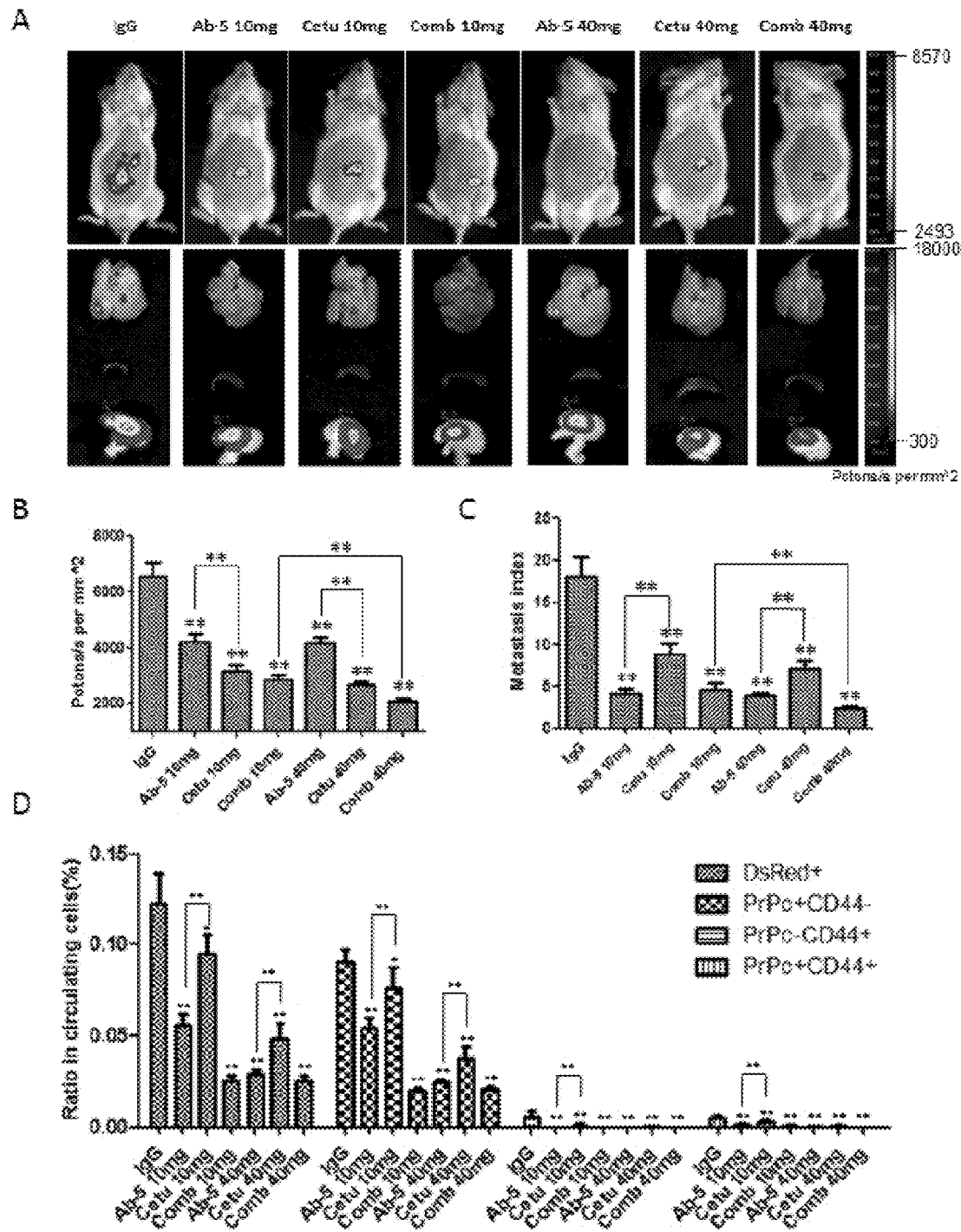
FIG. 9: Treatment with Ab-5 and cetuximab in combination could better inhibit growth of tumor in situ and tumor metastasis; A. fluorescence of abdominal tumors and fluorescence of visceral organs of mice treated alone or in combination; B. tumor sizes in mice treated alone or in combination; C. tumor metastasis in mice treated alone or in combination; D. tumor cell typing.

After tumor inoculation for 3 weeks, we started to perform treatment by injection of antibody, and after treatment for 8 weeks, the control group showed obvious ascetic fluid, and a living imaging instrument was used for collecting fluorescence information of abdominal tumor and fluorescence data of isolated organs after anatomy in mice. After treatment for 8 weeks, the mice of 6 groups treated with antibodies alone or in combination showed fluorescences of abdominal tumors (FIG. 9A, the first row), the fluorescence of isolated cecal tumor in situ and the fluorescence strength and points of liver metastatic tumor (FIG. 9A, the second row) were all significantly lower than that of IgG control group, and the differences in data were particularly significant (P<0.01); in addition, the mice of two combined treatment groups with different dosages showed significant difference in net photon number of tumor in situ (P<0.01), this indicated that high dose gave better effects than low dose (FIG. 9B). The analysis results showed that the treatment groups 2)~7) all had lower tumor metastatic indexes that the IgG control group, and the differences in data were particularly significant (P<0.01), the Ab-5 group administrated with the same dose had a tumor metastatic index lower than the Cetuximab group (P<0.01), which indicated that Ab-5 could better inhibit metastasis of tumor stem cells. Furthermore, the mice of two groups administrated with different doses had significantly different tumor metastatic indexes (P<0.01) (FIG. 9C).

From eyeball of a tumor-bearing mouse of the treatment group, 700 µL of blood sample was collected, stained with PrPc and CD44 antibody, and subjected to flow cytometer analysis. The data showed that all treatment groups had lower ratios of DsRed positive cells in comparison with the IgG control group, and the Ab-5 group administrated with the same dose had a lower ratio of DsRed positive cells in comparison with the Cetuximab group (P<0.01). In addition, the mice of two combined treatment groups administrated with different doses all had significantly decreased number of DsRed positive cells (FIG. 9D, DsRed+).

Further analysis of DsRed+ cell population showed:

(1) the IgG control group had the highest ratio of PrPc+ CD44− cells, while the differences between the treatment groups and the control group were highly significant (P<0.01), and showed similar trend as the DsRed+ cell ratios, which indicated that the most of DsRed+ cells were PrPc+CD44− cells. The Ab-5 group administrated with same dose had a lower ratio of PrPc+CD44− cells in comparison with the Cetuximab group (P<0.01), which indicated that Ab-5 had more potency in inhibiting migration of tumor in situ to peripheral blood system (FIG. 9D, PrPc+CD44−);

(2) in DsRed+ cell population, the ratio of PrPc-CD44+ cells in the IgG control group was very small. The statistic results showed that the ratios of PrPc-CD44+ cells in all antibody treatment groups were lower than that of the control group, and the differences were highly significant (P<0.01), and the Ab-5 group administrated with the same dose (10 mg/kg) had a lower ratio of PrPc-CD44+ cells in comparison with the Cetuximab group (P<0.01), and this trend was similar to those of the aforementioned two cell populations (FIG. 9D, PrPc-CD44+);

(3) the ratio of PrPc+CD44+ cells was very small as well, all antibody treatment groups had ratios of PrPc+CD44+ cells lower than that of the control group, and the results also showed highly significant differences (P<0.01), and the Ab-5 group administrated with the same dose (10 mg/kg) had a ratio of PrPc+CD44+ cells lower than the Cetuximab group (P<0.01), which indicated that Ab-5 was more potent in inhibiting metastasis of PrPc+CD44+ stem cells of tumor in situ (FIG. 9D, PrPc+CD44+).

The above results showed that the Ab-5 antibody of the present invention in combination with cetuximab could better inhibit growth and metastasis of tumors.

Embodiment 9. Transcription Factor Twist1 Had a Decreased Expression Quantity in Tumor Cells Treated with Ab-5

Figure 10:
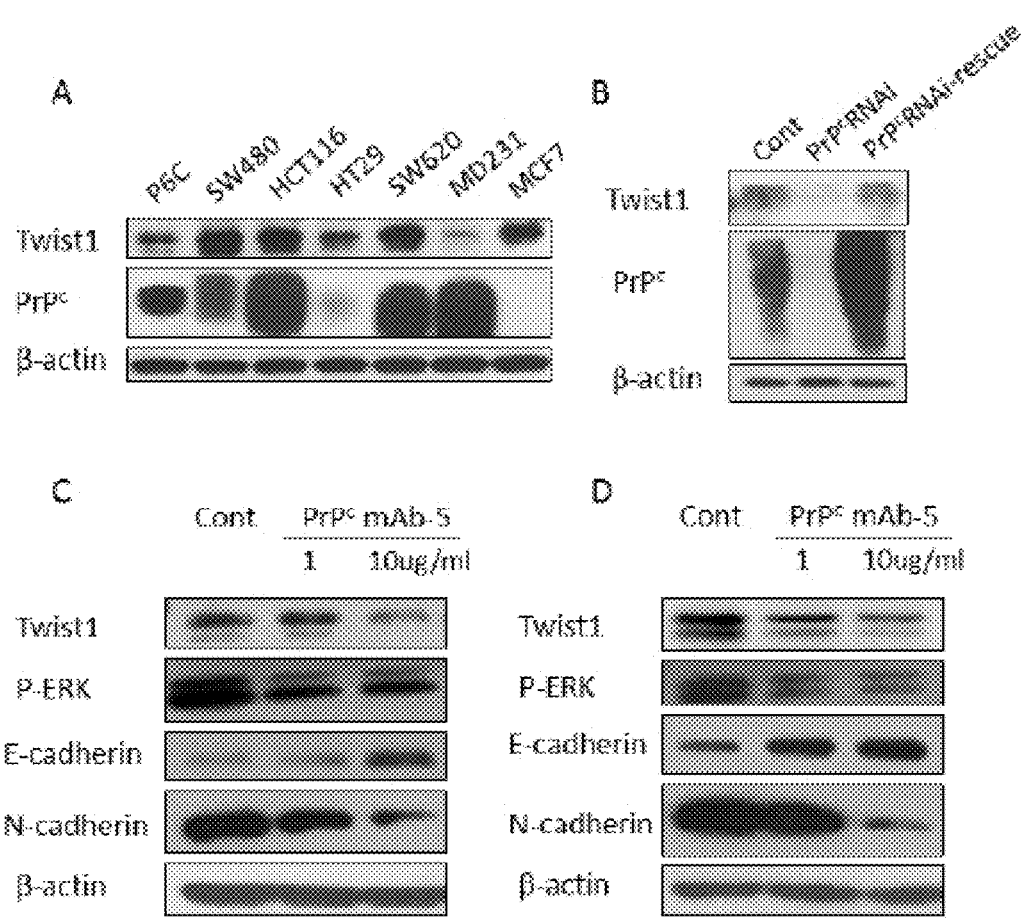
FIG. 10: Expression quantity of transcription factor Twist1 decreased in tumor cells treated by Ab-5: A. expression levels of transcription factor Twist1 in a plurality of tumor cell lines; B. PrPc protein and Twist1 expression quantity were in positive correlation in P6C cells; C. Twist1 in P6C cells and state factors of mesenchymal cells and epithelial cells changed along with Ab-5 antibody treatment; D. Twist1 in SW480 cells and state factors of mesenchymal cells and epithelial cells changed along with Ab-5 antibody treatment.

In order to further verify the specific action mechanism of Ab-5 antibody in inhibiting migration of PrPc positive cells, we detected the expression of transcription factor Twist1 related to migration in many tumor cell lines, and found that this protein was highly expressed in most of the cell lines, and in positive correlation with the PrPc expression level (FIG. 10A, except PrPc negative cells such as HT29 and MCF7, as well as Twist1 negative cells such as MD231).

In order to verify their relationship, we constructed PrPc siRNA plasmid, and the method for constructing the plasmid comprised:

The online program (http://i.cs.hku.hk/~sirna/software/sirna.php) was used to design and synthesize a RNAi primer aiming at specific PrP gene and corresponding Scramble primer:

PrP-RNAi: S: SEQ ID NO: 49:
5'-GATCCGCCGAGTAAGCCAAAAACCTTCAAGAGAGGTTTTTGGCTTA

CTCGGCTTTTTTGGAAA-3'

AS: SEQ ID NO: 50:
5'-AGCTTTTCCAAAAAAGCCGAGTAAGCCAAAAACCTCTCTTGAAGGT

TTTTGGCTTACTCGGCG-3'

PrP$^c$-Scramble: S: SEQ ID NO: 51:
5'-GATCCGCGCAGGATACGCAACACACCTCAAGAGAGTGTGTTGCGTA

TCCTGCGTT TTTTGGAAA-3'

AS: SEQ ID NO: 52:
5'-AGCTTTTCCAAAAAACGCAGGATACGCAACACACTCTCTTGAGG

TGTGTTGCGTATCCTGCGCG-3'

1. Two short hairpin RNA encoding complementary single strand oligonucleotide primers, were separately subjected to gradient annealing and pairing;

2. The annealed and paired primers were linked to pSilencer 2.1-U6 vector (digested with BamHI and HindIII endonucleases and recovered);

3. The linked product was transformed, when sequencing results were correct, it was cultured in large scale, and plasmids were extracted for standby use.

When the expression of PrPc protein in P6C cells were lowered by using RNAi function, the expression level of Twist1 decreased as well, and when the expression level of PrPc was regained, the expression of Twist1 was recovered as well, so that they showed an expression regulation relationship, i.e., the expression level of Twist1 changed with the level of PrPc in positive correlation (FIG. 10B). In the meantime, when P6C cells were treated in vitro with Ab-5 in different concentrations, it was found after 24 h that the expression level of Twist1 protein decreased, and was in direct proportion to the dose of Ab-5, and Twist1 downstream signal protein P-ERK also showed a decreased expression level with the increase of Ab-5 concentration, meanwhile epithelial cell marker E-cadherin expression increased, mesenchymal cell marker N-cadherin expression decreased, which indicated that with the decrease of expression level of Twist1, the cells were prone to changing from mesenchymal state to epithelial state, and their own migration ability decreased (FIG. 10C), which explained in some extent the reason why PrPc positive cells got a decreased migration ability after Ab-5 treatment. The similar results were also observed in another PrPc positive tumor cell, SW480 cells (FIG. 10D).

Finally, it should be declared that the above examples are merely used to help those skilled in the art to understand the present invention, rather than to limit the protection scope of the present invention, and any relevant technical solutions obtainable by those skilled in the art according to general technical knowledge and common knowledge fall within the protection scope of the present invention.

What is claimed is:

1. A monoclonal Ab-5 antibody, which specifically binds to human cellular prion protein (PrPc).

2. A kit for detecting PrPc protein comprising the monoclonal Ab-5 antibody of claim 1.

3. The monoclonal Ab-5 antibody of claim 1, having a light chain variable region (VL) comprising the amino acid sequence of SEQ ID NO:1, and a heavy chain variable region (VH) comprising the amino acid sequence of SEQ ID NO:2.

4. An active fragment of the antibody of claim 3, wherein the active fragment comprises: a single chain antibody, an antibody Fab region, or an antigen-binding fragment.

5. A kit for detecting PrPc protein comprising the active fragment of claim 4.

6. An antitumor drug, comprising the monoclonal Ab-5 antibody of claim 1.

7. A synergistic adjuvant for an antitumor drug, comprising the monoclonal Ab-5 antibody of claim 1.

8. The synergistic adjuvant of claim 7, wherein the antitumor drug is cetuximab.

* * * * *